US006080784A

United States Patent [19]
Driedger et al.

[11] Patent Number: 6,080,784
[45] Date of Patent: *Jun. 27, 2000

[54] PROTEIN KINASE C MODULATORS N

[75] Inventors: Paul E. Driedger, Boston; James Quick, Lexington, both of Mass.

[73] Assignee: Procyon Pharmaceuticals, Inc., Woburn, Mass.

[*] Notice: This patent is subject to a terminal disclaimer.

[21] Appl. No.: 08/480,251

[22] Filed: Jun. 7, 1995

Related U.S. Application Data

[63] Continuation-in-part of application No. 07/664,396, Mar. 4, 1991, which is a continuation-in-part of application No. 07/537,885, Jun. 14, 1990, abandoned, which is a continuation-in-part of application No. 07/061,299, Jun. 10, 1987, abandoned, which is a continuation-in-part of application No. 06/872,812, Jun. 11, 1986, abandoned, application No. 07/559,296, Jul. 30, 1990, abandoned, and application No. 07/559,701, Jul. 30, 1990, Pat. No. 5,145,842, which is a division of application No. 07/322,881, Mar. 13, 1989, abandoned, which is a continuation-in-part of application No. 07/061,299, Jun. 10, 1987, abandoned, and a continuation-in-part of application No. 08/120,643, Sep. 13, 1993, Pat. No. 5,643,948, which is a continuation-in-part of application No. 07/664,397, Mar. 4, 1991, abandoned, which is a continuation-in-part of application No. 07/322,881.

[51] Int. Cl.[7] .......................... A61K 31/22; A61K 31/23; A61K 31/235; A61K 31/075

[52] U.S. Cl. .......................... 514/546; 514/63; 514/480; 514/490; 514/512; 514/532; 514/533; 514/544; 514/552; 552/227; 552/229; 556/449; 556/482; 558/272; 558/276; 560/32; 560/33; 560/102; 560/105; 560/107; 560/162; 560/249; 560/256; 568/659; 568/660; 568/671; 568/680

[58] Field of Search .................................. 560/162, 249, 560/32, 33, 102, 105, 107, 256; 558/272, 276; 514/63, 480, 490, 512, 532, 544, 546, 552, 719, 729; 552/227, 229; 556/449, 482; 568/659, 660, 671, 680

[56] References Cited

U.S. PATENT DOCUMENTS

| | | | |
|---|---|---|---|
| 4,376,821 | 3/1983 | Braude | 435/68 |
| 4,376,822 | 3/1983 | Braude | 435/68 |
| 4,401,756 | 8/1983 | Gillis | 435/68 |
| 4,460,685 | 7/1984 | Vilcek et al. | 435/70 |
| 4,716,179 | 12/1987 | Hecker et al. | 514/691 |
| 5,089,517 | 2/1992 | Choi et al. | 514/411 |
| 5,145,842 | 9/1992 | Driedger et al. | 515/63 |
| 5,643,948 | 7/1997 | Driedger et al. | 514/533 |
| 5,716,968 | 2/1998 | Driedger et al. | 514/323 |
| 5,750,568 | 5/1998 | Driedger et al. | 514/533 |

FOREIGN PATENT DOCUMENTS

| | | | |
|---|---|---|---|
| 87/07599 | 12/1987 | WIPO | A61K 31/00 |

OTHER PUBLICATIONS

Dunn, J.A. and Blumberg, P.M., "Specific Binding of [20-³H]12–Deoxyphorbol 13–Isobutyrate to Phorbol. Ester Receptor Subclasses in Mouse Skin Particulate Preparations," *Cancer Res. 43*: 4632–4637 (Oct. 1983).

Sugimura, T., "Potent Tumor Promoters Other Than Phorbol Ester and Their Significance," *Gann 73*(4): 499–507 (Aug. 1982).

Hecker, E. and Schmidt, R., "Phorbolesters—The Irritants and Cocarcinogens of *Croton Tiglium* L.," *Fortschritte D. Chemie Organischer Naturstoffe 31*: 377–467 (1974).

Evans, F.J. and Soper, C.J., "The Tigliane, Daphnane and Ingenane Diterpenes, Their Chemistry, Distribution and Biological Activities. A Review," *Lloydia 41*(3): 193–233 (May–Jun. 1978).

Schmidt, R. and Hecker, E., "Untersuchungen über die Beziehungen zwischen Struktur und Wirkung von Phorbolestern," In: Lettré and G. Wagner (eds.), *Aktuelle Probleme aus dem Gebiet der Cancerologie III*, Third Heidelberg Symposium, pp. 98–108. Berlin: Springer Verlag, 1971.

Kupchan, S. et al. "Antileukemic Principles Isolated from Euphorbiaceae Plants," *Science 191*: 571–572 (Feb. 1976).

Fürstenberger, G. et al., "New Highly Irritant Euphorbia Factors from Latex of *Euphorbia tirucalli* L.," *Experientia 33*: 986–988 (Feb. 15, 1977).

Thielmann, H.W. and Hecker, E., "Die Flaschenträger Reaktion," *Liebigs Ann. Chem. 728*: 158–183 (1969).

Thielmann, H.-W. and Hecker, E., "Beziehungen zwischen der Struktur von Phorbolderivaten und ihren entzündlichen . . . " In: C.G. Schmidt and O. Wetter (eds.), *Forschritte der Krebsforschung* vol. VII, pp. 171–179, NY; Schattauer (1969).

Hecker, E., "Structure–Activity Relationships in Diterpene Esters Irritant and Cocarcinogenic to Mouse Skin," In: T.J. Slaga, A. Sivak and R.K. Boutwell (eds.), *Carcinogenesis 2. Mechanisms of Tumor Promotion and Cocarcinogenesis*:11–48, NY; Raven Press (1978).

Schmidt, R. and Evans, F., "Skin Irritant Effects of Esters of Phorbol and Related Polyols," *Arch. Toxicol. 44*: 279–289 (1980).

Adolf, W. and Hecker, E., "On the Active Principles of the Thymelaeaceae", *J. Med. Plant Res. 45*: 177–182 (1982).

Jeffrey, A. and Liskamp, R., "Computer–Assisted Molecular Modeling of Tumor Promoters: Rationale for the Activity of Phorbol Esters, Teleocidin B, and Aplysiatoxin," *Proc. Natl. Acad. Sci. USA 83*: 241–245 (Jan. 1986).

Evans, F.J., "Phorbol: Its Esters and Derivatives," In: F.J. Evans (ed.), *Naturally Occuring Phorbol Esters*, pp. 171–215. CRC Press (1986).

Nishizuka, Y., "The Role of Protein Kinase C in Cell Surface Signal Transduction and Tumour Promotion," *Nature 308*: 693–698 (Apr. 19, 1984).

Driedger, P. and Blumberg, P., "Quantitative Correlation Between in Vitro and in Vivo Activities of Phorbol Esters," *Cancer Research 39*: 714–719 (Mar. 1979).

(List continued on next page.)

*Primary Examiner*—Richard L. Raymond
*Attorney, Agent, or Firm*—Hamilton, Brook, Smith & Reynolds, P.C.

[57] ABSTRACT

Compositions with protein kinase C-modulatory, anti-inflammatory and other activities are disclosed.

23 Claims, No Drawings

OTHER PUBLICATIONS

Driedger, P. and Blumberg, P., "The Effect of Phorbol Diesters on Chicken Embryo Fibroblasts," *Cancer Research* 37: 3257–3265 (Sep. 1977).

Ganong, B., et al., "Specificity and Mechanism of Protein Kinase C Activation by sn–1,2–diacylglycerols," *Proc. Natl. Acad. Sci. USA 83*: 1184–1188 (Mar. 1986).

Schmidt, R. and Hecker, E., "Simple Phorbol Esters as Inhibitors of Tumor Promotion by TPA in Mouse Skin," *Carcinogenesis 7*: 57–63 (1982).

Marshall, G.T. and Kinghorn, A.D., "Short–Chain Phorbol Ester Constituents of Croton Oil," JAOCS, 61(7): 1220–1225 (Jul. 1984).

Aldaz, C.M et al., "Cutaneous Changes During Prolonged Application of 12–O–tetradecanoylphorbol 13–acetate on Mouse Skin and Residual Effects after Cessation of Treatment," (From *Chem. Abstracts*, 1985 45(6) 103: 136798).

Baxter, C.S. et al., "Interaction of Tumor–Promoting Agents with Immunofunctional Cells in In Vitro and In Vivo," (From *Chem. Abstracts*, 1994, 103: 136812).

PROTEIN KINASE C MODULATORS N

RELATED APPLICATIONS

This application is:
(i) a continuation-in-part of application Ser. No. 07/664,396, filed Mar. 4, 1991, which is a continuation-in-part of:
  (a) application Ser. No. 07/537,885, filed Jun. 14, 1990 (abandoned), which is a file-wrapper continuation-in-part of application Ser. No. 07/061,299, filed Jun. 10, 1987 (abandoned), which is a continuation-in-part of application Ser. No. 06/872,812, filed Jun. 11, 1986 (abandoned); and
  (b) application Ser. No. 07/559,296, filed Jul. 30, 1990 (abandoned) and application Ser. No. 07/559,701, filed Jul. 30, 1990 (now U.S. Pat. No. 5,145,842, issued Sep. 8, 1992), which are, respectively, a division and a continuation-in-part of application Ser. No. 07/322,881, filed Mar. 13, 1989 (abandoned), which is a division of application Ser. No. 07/061,299, filed Jun. 10, 1987 (abandoned); and
(ii) a continuation-in-part of application Ser. No. 08/120,643, filed Sep. 13, 1993, now U.S. Pat. No. 5,643,948, which is a continuation-in-part of application Ser. No. 07/664,397 filed Mar. 4, 1991 (abandoned);

all of which are herein incorporated by reference in their entirety.

BACKGROUND

Protein kinase C (also known as "calcium/phospholipid-dependent protein kinase", "PKC" or "C-kinase") is a family of closely related enzymes; one or more members of the protein kinase C family are found in nearly all animal tissues and animal cells that have been examined. The identity of protein kinase C is generally established by its ability to phosphorylate certain proteins when adenosine triphosphate and phospholipid cofactors are present, with greatly reduced activity when these cofactors are absent. Protein kinase C is believed to phosphorylate only serine and/or threonine residues in the proteins that are substrates for protein kinase C. Additionally, some forms of protein kinase C require the presence of calcium ions for maximal activity.

Protein kinase C comprises a family of ten or more closely related protein molecules [Parker, P. J. et al. *Mol. Cell. Endocrin.* 65: 1–11 (1989)]. Because of their high degree of relatedness they are referred to as "isozymes", "isotypes" or "isoforms". Occasionally the term "subtypes" is used, but this term is usually reserved to designate, as a subdivision, two or more variants of a single isotype.

The currently known isotypes of protein kinase C are: α, $\beta_1$, $\beta_2$ and γ (the "A-group"); δ, ε, ε' [Ono, Y. et al., *J. Biol. Chem.* 263: 6927–6932 (1988)], η [also known as protein kinase C-L; Osada, S. et al., *J. Biol. Chem.* 265: 22434–22440 (1990) and Bacher, N. et al., *Mol. Cell. Biol.* 11: 126–133 (1991), respectively], and θ [Osada, S.-I. et al., *Mol. Cell. Biol.* 12: 3930–3938 (1992) (the "B-group"); ζ [Ono, Y. et al., *J. Biol. Chem.* 263: 6927–6932 (1988)] and ι [Selbie, L. A. et al., *J. Biol. Chem.* 268: 24296–24302 (1993), the latter also being known as PKCλ [Akimoto, K. et al., *J. Biol. Chem.* 269: 12677–12683 (1994)] (the "C-group"); and μ [Johannes, F.-J. et al., *J. Biol. Chem.* 269: 6140–6148 (1994)], also known as PKD [Valverde, A. M. et al., *Proc. Natl. Acad. Sci USA* 91: 8572–8576 (1994) (the "D-group"). Members of the A-group require calcium ions for maximal activation, whereas the B-, C- and D-group members are thought to be largely calcium-independent for activation. The genes for each of the isotypes above have been cloned from one or more animal and yeast species and the clones have been sequenced; the relatedness of the genes and their product polypeptides is thus well established.

Beyond the ability of phospholipid and, for some isotypes, calcium to stimulate protein kinase C activity, members of the A-, B- and D-groups of the protein kinase C family are also substantially stimulated by certain 1,2-sn-diacylglycerols that bind specifically and stoichiometrically to a recognition site or sites on the enzyme. This site is called the diacylglycerol binding site, and it is located on the amino-terminal portion of protein kinase C, the so-called "regulatory domain". The carboxy-terminal portion of protein kinase C carries the site at which protein phosphorylation is effected, and this portion is therefore called the "kinase domain".

Thus, the rate at which various protein kinase C family members carry out their enzymatic phosphorylation of certain substrates can be markedly enhanced by the presence of the cofactors such as phospholipids, diacylglycerols (except for the C-group) and, for some protein kinase C family members, calcium ions. This stimulation of protein kinase C activity is referred to as protein kinase C "activation", and the activation of protein kinase C by the binding of diacylglycerols to the regulatory domain of protein kinase C is of particular importance in the normal and pathological functions of protein kinase C.

In contrast to the activation of protein kinase C, some chemical compounds have been shown, when added to protein kinase C enzyme assays, to reduce the rate at which protein kinase C phosphorylates its substrates; such compounds are referred to as protein kinase C "inhibitors" or, in some cases, "antagonists". In some circumstances, protein kinase C inhibitors are capable of inhibiting various cellular or tissue phenomena which are thought to be mediated by protein kinase C.

Activation of protein kinase C by diacylglycerols has been shown to be an important physiological event that mediates the actions of a wide variety of hormones, neurotransmitters, and other biological control factors such as histamine, vasopressin, α-adrenergic agonists, dopamine agonists, muscarinic cholinergic agonists, platelet activating factor, cytokines, growth factors and many others [see Y. Nishizuka, *Nature* 308: 693–698 (1984) and *Science* 225: 1365–1370 (1984) for reviews].

The biological role of protein kinase C is also of great interest because of the discovery that certain very powerful tumor promoting chemicals activate this enzyme by binding specifically and with very high affinity to the diacylglycerol binding site on the enzyme. In addition to diacylglycerols, there are at present six other known classes of compounds that bind to this site: diterpenes such as the phorbol esters; indole alkaloids (indolactams) such as the teleocidins, lyngbyatoxin, and indolactam V; polyacetates such as the aplysiatoxins and oscillatoxins; certain derivatives of diaminobenzyl alcohol; macrocyclic lactones of the bryostatin class; and, benzolactams such as (−)-BL-V8-310; these seven classes of compounds are collectively referred to herein as "phorboids". The phorbol esters have long been known as powerful tumor promoters, the teleocidins, aplysiatoxins, diacylglycerols and, though weak, the bryostatins are now known to have this activity, and it appears likely that additional classes of compounds will be found to have the toxic and tumor promoting activities associated with the capability to bind to the diacylglycerol site of protein kinase C and thus activate the enzyme. Other toxicities of these agents when administered to animals include lung injury and profound changes in blood elements, such as leukopenia and neuropenia, among many others.

Representative examples of the diterpene class of previously known protein kinase C-activating compounds are depicted below:

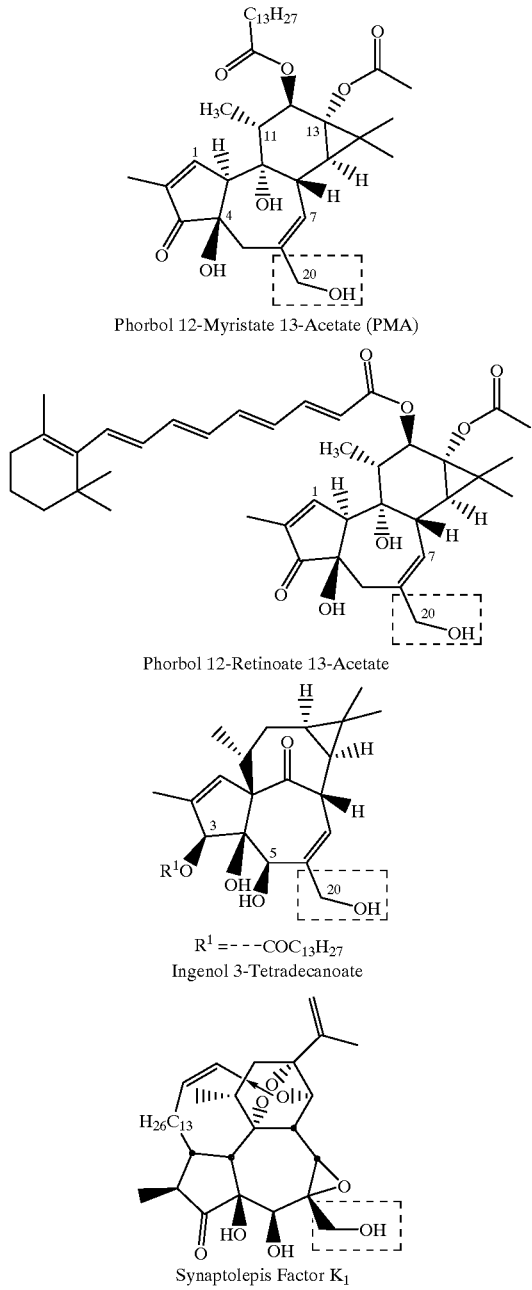

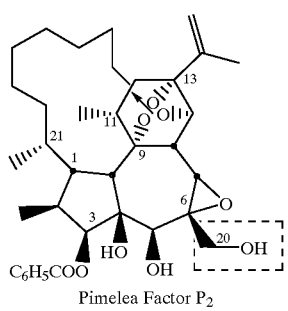

Pimelea Factor P$_2$

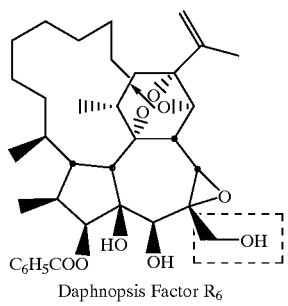

Daphnopsis Factor R$_6$

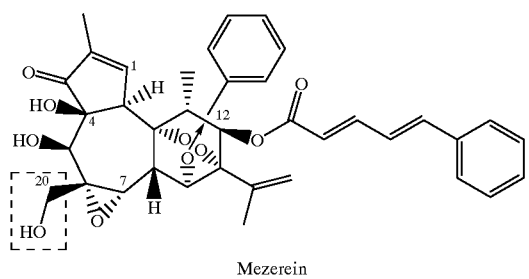

Mezerein

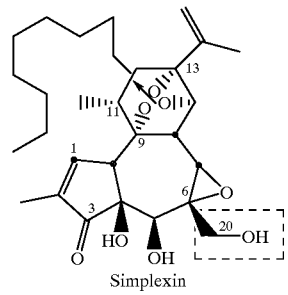

Simplexin

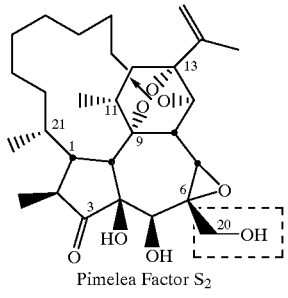

Pimelea Factor S$_2$

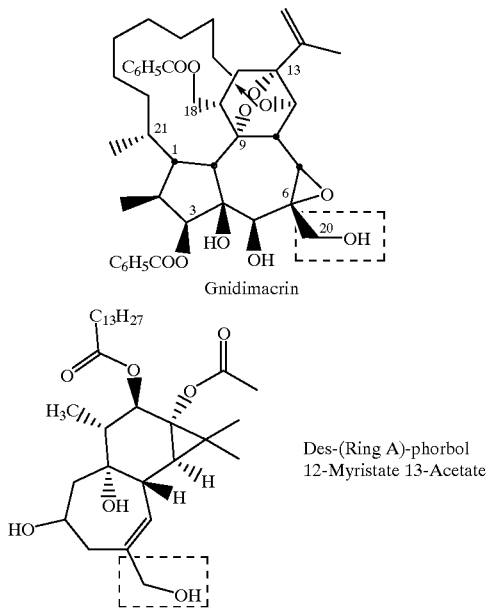

Gnidimacrin

Des-(Ring A)-phorbol 12-Myristate 13-Acetate

It can be seen that the phorboids depicted have diverse structural elements of both hydrophilic and hydrophobic nature, with one prominent exception, namely that each contains a hydroxymethyl or 1-hydroxyethyl group (indicated by the dashed-line boxes in each structure). Among the seven classes the diterpenes, indolactams, polyacetates, bryostatins and benzolactams have members of especially high potency, in the range of low nanomolar affinities for protein kinase C.

In addition to potent tumor promoting activity, these seven classes of compounds display a vast range of biological activities, as would be expected from the widespread distribution of their target enzyme. Many of these activities indicate the involvement of protein kinase C in important normal or pathological processes in animals, as shown by experiments utilizing both genetic and pharmacological approaches. Thus, the phorboids are potent skin inflammatory agents, cause smooth muscle contraction in several tissues, alter immune system function and can be used to cause or mimic a wide variety of other normal or pathological biological responses. Published evidence indicates that disease states such as the development of cancer, the onset and/or maintenance of inflammatory disease, the role of vasoconstriction in hypertension, the role of bronchoconstriction in asthma, the life cycles of many pathogenic human viruses, and the role of certain classes of cholinergic, adrenergic, serotoninergic and dopaminergic synapses in diseases of the central/peripheral nervous systems, may be mediated in vivo by the stimulation of protein kinase C or other diacylglycerol binding site-bearing entities by diacylglycerols, the latter being generated in the cell by either normal physiological or by pathological agents or conditions.

In analyzing the activity of a pharmaceutical or other bioactive compound, it is useful to consider two properties: the efficacy of the compound, defined as the capability to elicit a full or partial biological result, such as complete displacement of a ligand from its receptor site or the complete inhibition of inflammation or edema caused by a standard stimulus; and the potency, defined as that amount or concentration of drug that causes 50% of the full response (often abbreviated as the $ED_{50}$). It is frequently the case within a given class of pharmaceutical agents that individual members of the class all have equal efficacy, i.e. they each can generate a full biological effect, but they show differing potencies. Thus, the structural modifications within such a class generally affect only the amount necessary to achieve a given result (i.e. the potency), and the modified compounds otherwise generally retain the same central biological characteristic (i.e. efficacy as a pharmaceutical or in a given biological assay or test). There may also be differences between members of such a class as regards properties other than the central biological characteristic; for example, members of the class might differ in side effects or susceptibility to metabolism by an organism.

Well-known pharmaceuticals that have been in extensive use for years or decades show a wide range of optimal therapueutic potencies. Aspirin, for example, is often taken in multi-gram amounts per day for treatment of inflammation or arthritis, and detailed analyses of its mechanism of action in vitro show that a concentration in the millimolar range is required for certain therapeutic effects of aspirin. In contrast, steroid-based topical anti-inflammatory compounds such as fluocinolone acetonide are many thousand-fold more potent, and, beyond this, some oral contraceptive agents are prescribed in daily doses in the microgram range. Thus, although high potency is generally advantageous for a pharmaceutical, it is not an absolute requirement.

The concepts of potency and efficacy provide a useful basis for understanding the properties of the nearly one thousand analogs of the typically skin-inflammatory and tumor-promoting phorboids that have been reported in the literature, including numerous examples on which major or minor chemical modifications have been made [see Evans and Soper, *Lloydia* 41: 193–233 (1978) and references cited therein]. When the structures of these phorboids are compared, and their activities for inflammation, tumor promotion and protein kinase C modulation are analyzed from the perspective of efficacy and potency, a remarkable unity is observed. To a degree that is nearly unique among known ligand-receptor phenomena, the structures of the different classes of phorboids vary quite markedly from one to the other class yet widespread testing of their biological activities has shown that these classes have essentially the same target site, namely the diacylglycerol binding site on protein kinase C, and generally have very similar biological properties. In particular, the numerous known phorboids of the diterpene, indolactam, diacylglycerol, polyacetate, bryostatin and benzolactam classes appear to have, with very minor exceptions, virtually identical efficacies as skin irritants and tumor promoters [T. Sugimura, *Gann*, 73: 499–507 (1982)]. Typical exceptions involve: (i) a few compounds that have a short duration of irritant activity and/or manifest diminished tumor promoting activity, perhaps due to slightly different protein kinase C isotype selectivity, toxicity or secondary parameters such as differing metabolic destruction rates; (ii) the bryostatins, which, though having weak but detectable inflammatory and tumor-promoting activity, show other, non-correlating pharmacological properties; or (iii) certain short-chain diesters of phorbol which are tumor promotion inhibitors at low doses but fully efficacious tumor promoters when tested alone at higher concentrations.

In contrast to the essentially equal efficacies among the vast majority of phorboids, their relative potencies cover a wide range, as measured in inflammation and promotion tests and as measured in numerous other in vivo and in vitro systems. Example compounds can be found in the diterpene, indolactam, polyacetate and benzolactam classes that have nearly equal, very high potencies. At the same time there are compounds in each of these classes which embody significant structural changes that do not diminish efficacy but do result in potency decreases of 10-fold to 100,000-fold or more [see, for example, Driedger and Blumberg, Cancer Res. 37: 3257–3265 (1977), Cancer Res. 39: 714–719 (1979)]. Thus, all these compounds appear to be capable of achieving generally the same biological results, and merely differ in the amount which must be used to obtain a given result.

In vitro measurements of biochemical properties provide an even more sensitive method for comparing the properties of the various phorboids. For example, using a radioactively labeled phorboid such as [$^3$H]phorbol 12,13-dibutyrate or [$^3$H]lyngbyatoxin, one can measure the potency of a test compound as a competitive ligand for the diacylglycerol binding site, which is also referred to herein as the "phorboid binding site" on protein kinase C or on other biological molecules which have phorboid binding sites (see below). Alternatively, one can measure the ability of a given phorboid to stimulate the protein kinase C-mediated incorporation of radioactive phosphate from [$^{32}$P]adenosine triphosphate into a standard acceptor substrate such as histone H1. These tests reveal a difference in potency between given phorboid agonists of as much as 10,000,000-fold or more [Dunn and Blumberg, Cancer Res. 43: 4632–4637 (1983), Table 1].

These basic data regarding the phorboid agonists are an important consideration because they underscore the concept that the structural differences among the phorboids known prior to the instant invention, especially the widely studied diterpenes, indolactams, diacylglycerols, polyacetates and bryostatins, generally do not affect their efficacies as toxic agonists, and indeed a remarkably wide variety of structural changes are tolerated in this regard. Such changes generally alter potency only and do not provide agents with therapeutic utility, since the resulting compounds retain their toxicity.

Some minor changes in phorboid structure are known to result in generally inactive compounds, such as a stereochemical change from 4-β to 4-α in the phorbol series, and indeed some of the diterpene skeleton structures carry hydroxy groups that must be esterified in order for inflammatory activity to be observed. However, these inactive compounds are quite few in number among the known phorboids, and no therapeutic utility has been demonstrated for them.

The phorbol esters, indolactams, polyacetates, diaminobenzyl alcohols, and bryostatins are generally found in plants, molds, and algae, or are synthetic in origin. Although they are found in many parts of the world, normal human contact with these classes of phorboids is thought to be low and of negligible medical significance. In contrast, the diacylglycerols are part of the functioning of virtually every type of animal cell, and the undesirable activation (and, alternatively as discussed below, the cessation of desirable activation) of protein kinase C by the diacylglycerols is thought to have a very widespread role in human diseases.

Thus, compounds capable of blocking the activation of, or inhibiting, protein kinase C by acting as specific pharmacological antagonists of the diacylglycerols at the diacylglycerol binding site on protein kinase C, would be valuable agents in the prevention and treatment of a wide variety of diseases in animals and humans. For example, the need for, and potential utility of, protein kinase C inhibitors/antagonists as agents for the treatment of cancer has received much attention [D. Corda, et al., Trends in Pharmacological Sciences 11: 471–473 (1990); G. Powis, Trends in Pharmacological Sciences 12: 188–194 (1991); S. Gandy and P. Greengard, Trends in Pharmacological Sciences 13: 108–113 (1992); B. Henderson and S. Blake, Trends in Pharmacological Sciences 13: 145–152 (1992)].

It is possible that the different protein kinase C isozymes have different biological roles, and published evidence supports this idea [Homan, E., Jensen, D. and Sando, J., J. Biol. Chem. 266: 5676–5681 (1991); Gusovsky, F. and Gutkind, S., Mol. Pharm. 39: 124–129 (1991); Borner, C., "The Role of protein kinase C in Growth Control", Sixth International Symposium on Cellular Endocrinology, W. Alton Jones Cell Science Center, Lake Placid, N.Y., Aug. 12–15, 1990; Naor, Z. et al., Proc. Natl. Acad. Sci. USA 86: 4501–4504 (1989); Godson, C., Weiss, B. and Insel, P., J. Biol. Chem. 265: 8369–8372 (1990); Melloni, E. et al., Proc. Natl. Acad. Sci. USA 87: 4417–4420 (1990); Koretzky, G. et al., J. Immunology 143: 1692–1695 (1989)]. For example, the stimulation of one protein kinase C isotype or a limited subset of protein kinase C isotypes might lead to undesirable results such as the development of inflammation [Ohuchi, K. et al., Biochim. Biophys. Acta 925: 156–163 (1987)], the promotion of tumor formation [Slaga, T., Envir. Health Perspec. 50: 3–14 (1983)] or an increased rate of viral replication in cells (i.e., de novo infection of cells and/or expression, assembly and release of new viral particles) [Harada, S. et al., Virology 154: 249–258 (1986)].

On the other hand, other protein kinase C isozymes might be responsible for the many beneficial effects observed when protein kinase C is stimulated by known protein kinase C activators in a variety of biological settings; such beneficial effects include the cessation of division of leukemic cells [Rovera, G., O'Brien, T. and Diamond, L., Science 204: 868–870 (1979)], multiplication of colonies of lymphocytes [Rosenstreich, D. and Mizel, S., J. Immunol. 123: 1749–1754 (1979)] and leucocytes [Skinnider, L. and McAskill, J., Exp. Hematol. 8: 477–483 (1980)] or the secretion of useful bioregulatory factors such as interferon-γ [Braude, I., U.S. Pat. No. 4,376,822] and interleukin-2 [Gillis, S., U.S. Pat. No. 4,401,756].

Recent publications indicate that diacylglycerol binding sites exist on newly-described proteins which lack the kinase domain, and thus lack the kinase activity, of protein kinase C. One such protein is n-chimaerin, found in human brain [Ahmed et al., Biochem. J. 272: 767–773 (1990)] and the other is the unc-13 gene product of the nematode Caenorhabditis elegans, [Maruyama, I. and Brenner, S., Proc. Natl. Acad. Sci. USA 88: 5729–5733 (1991)]. The presence of the diacylglycerol binding sites on these two proteins was demonstrated by standard binding experiments with [$^3$H] phorbol 12,13-dibutyrate. These new proteins may have other enzymatic or biological activities which can be modulated by compounds which bind to their diacylglycerol binding sites. Thus, such compounds may have utility on non-protein kinase C biological targets.

Given that there are now numerous distinct biological entities bearing diacylglycerol binding sites, it would be highly desirable to obtain chemical compounds which could specifically and selectively target one or another type of diacylglycerol binding site, thus permitting one to selectively activate or inhibit one such site without affecting the others. Such compounds would be valuable experimental tools for studying the role of individual types of proteins bearing diacylglycerol binding sites as well as providing novel means for treating diseases in which protein kinase C or other diacylglycerol binding site-bearing proteins are involved.

There are several published reports describing chemical compounds capable of selectively distinguishing several diacylglycerol/phorboid-type binding sites in mouse skin [Dunn and Blumberg, op. cit.] and in purified preparations of protein kinase C isotypes [Ryves, W. J., et al., *FEBS Letters* 288: 5–9(1991)]. However, in these studies, even the compounds showing the clearest differences in affinity for these distinct classes, namely phorbol 12,13-dibutyrate, 12-deoxyphorbol 13-isobutyrate, 12-deoxyphorbol 13-phenylacetate and thymeleatoxin, are only selective by a factor of 10–1000 in dissociation constant among the different binding sites. Furthermore, these compounds have potent skin inflammatory activity and are not desirable in human or animal medicine because of this toxicity.

Thus, to briefly recapitulate, two kinds of new compounds relating to diacylglycerol binding sites would be highly desirable. The first type would be capable of selectively activating one or a few useful, but not other, deleterious, diacylglycerol binding site-bearing targets. The second type would be capable of inhibiting, or antagonizing the stimulation of, one or more diacylglycerol binding site-bearing targets without blocking activity and/or activation of phorboid-activated target entities whose activation is physiologically harmless or desirable. These kinds of compounds would be valuable agents for the study of diacylglycerol binding site-bearing entities and for the prevention or treatment of a wide range of human and animal diseases thought to involve protein kinase C or other entities under the control of diacylglycerol binding sites.

The physiology of protein kinase C includes, in certain cases, a phenomenon known as "down-regulation", manifested as the ability of protein kinase C activators of the phorboid class to initially stimulate protein kinase C at or shortly after the time of application of the phorboid, followed by a net, phorboid-induced metabolic lowering of total protein kinase C levels. [See e.g. Cooper, D. R. et al., *Biochem. Biophys. Res. Comm.* 161: 327–334 (1989); Isakov, N. et al., *J. Biol. Chem.* 265: 2091–2097 (1990); Strulovici, B. et al.,*J. Biol. Chem.* 266: 168–173 (1991); and Gschwendt, M. et al., *FEBS Letters* 307: 151–155 (1992). Several of these studies illustrate the selective down-regulation of one but not another protein kinase C isotype via extended exposure to standard protein kinase C-activating phorboids such as phorbol esters.] Thus, at short times the phorboids generally act as protein kinase C stimulants, but at longer times, for certain protein kinase C isotypes in certain biological settings, the net loss of one or more protein kinase C isotypes in response to the (initially stimulatory) phorboid results in substantial or complete loss of the protein kinase C. This important effect is therefore functionally equivalent to inhibition of protein kinase C, even though the effect is achieved by nominal activators of this enzyme family, and it is clear that, on a long-term time scale, net inhibition of protein kinase C can be achieved either with inhibitors or, in many cases, activators of protein kinase C. A given compound might therefore show quite complex properties on protein kinase C; for example, a non-toxic agonist might fail to stimulate the protein kinase C isotype(s) responsible for inflammation while at the same time activating many other isotypes on a short time scale and inhibiting a subset of the latter isotypes on a long time scale.

With the exception of clinical tests of bryostatin 1 itself [Prendiville, J. et al., *Brit. J. Cancer* 68: 418–424 (1993)] and of certain modifications to the hydroxymethyl/1-hydroxyethyl group present in all currently known phorboids [P. E. Driedger and J. Quick, U.S. Pat. No. 5,145,842 and related patents and patent applications], efforts to make medical use of the previously known phorboids themselves or to modify the structures of these known phorboids in medically useful ways, have generally not been successful in producing useful compounds with toxicity low enough for use in humans.

For example, it has been known for some time that several of the toxic, inflammatory and tumor-promoting compounds such as phorbol 12-tigliate 13-decanoate, mezerein, lynobyatoxin and aplysiatoxin have anti-leukemic activity in mouse model tests [T. Sugimura, op cit.; S. M. Kupchan and R. L. Baxter, *Science* 187: 652–653 (1975); S. M. Kupchan, et al., *Science* 191: 571–572 (1976); M. C. Territo and H. P. Koeffler, *Br. J. Haematol.* 47, 479–483 (1981)]. However, these compounds are all extremely toxic to many tissues and are cancer suspect agents, making them quite unattractive for consideration as human therapeutic agents.

Ganong, et al. [*Proc. Nat. Acad. Sci. USA* 83: 1184–1188 (1986)] tested a series of diacylglycerols and found no antagonistic activity in that series against the standard agonist, 1,2-dioctanoylglycerol. Compounds tested in this work were modified in the hydroxymethyl or other portions of the diacylglycerol molecule, and these modifications produced only a loss of activity or a weakened activity that was not distinguishable from the agonist activity of 1,2-dioctanoylglycerol itself, a compound which is toxic to mouse skin [R. Smart, et al., *Carcinogenesis* 7: 1865–1870 (1986); A. Verma, *Cancer Res.* 48: 2168–2173 (1988)]. These modified diacylglycerols were not antagonists in these tests and no utility was found. Schmidt and Hecker ("Simple phorbol esters as inhibitors of tumor promotion by TPA in mouse skin". *Carcinogenesis,* Vol. 7, ed. by E. Hecker et al., Raven Press, New York, 1982, pp. 57–63) studied the abilities of a series of diterpene phorboids to inhibit tumor promotion by the standard phorboid agonist tumor promoter phorbol 12-myristate 13-acetate (PMA, also known as TPA). They found that, at low doses, some short-chain ester derivatives of phorbol, differing from PMA only in the chain length of the 12- and 13-ester substituents were able to block the tumor promotion by PMA. However, all of the compounds that were active as antagonists at low doses are also known to be very efficacious skin irritants themselves at slightly higher doses and most of them are also known to have tumor promoting activity. Thus, these short-chain esters still have toxic inflammatory and tumor promoting activity at doses only slightly different from those which would be needed to exhibit a therapeutic effect in mice. In the same study (Schmidt and Hecker, op. cit.) phorbol 12-myristate (abbreviated "TP" in the Schmidt and Hecker publication), which differs from PMA only in the lack of a substituent on the 13-hydroxy group, was tested as an inhibitor of tumor promotion and was found to be inactive.

SUMMARY OF THE INVENTION

It has now been found that compounds of the diterpene class, with the usual hydroxymethyl or 1-hydroxyethyl group intact and having at least one substituent other than hydrogen or hydroxy at carbon 12 (common phorbol numbering) and a generally polar group, as exemplified, without limitation, by hydroxy, amino, thiol, hydroxymethyl, mercaptomethyl, aminomethyl, 2-hydroxyethyl, carboxy, unsubstituted carboxamido, or unsubstituted aminocarbonyloxy group in the α configuration at carbon 13, not only lack the inflammatory activity of other members of the diterpene class of phorboids but also have useful activities as anti-inflammatory, anti-cancer, anti-HIV, anti-psoriatic agents, as agents to treat numerous other diseases involving protein kinase C and as modulators of protein kinase C. Thus, in this very unusual case a minor change in the chemical structure of diterpene-type phorboids at a location other than the hydroxymethyl leads to a very substantial and useful change in biological properties. This is in contrast to the previous belief, based on published experimental results [Thielmann, H.-W. and Hecker, E., "Beziehungen zwischen der struktur von phorbolderivaten und ihren entzundlichen und tumorpromovierenden eigenschaften." Fortschr. Krebsforsch. 7: 171–179 (1969)], that diterpenes such as phorbol 12-decanoate, phorbol 12-dodecanoate and phorbol 12-myristate are biologically inactive, and it is especially in contrast to the usual association of the presence of hydroxymethyl or 1-hydroxyethyl groups with proinflammatory activity.

This invention provides compounds with a range of protein kinase C-modulatory properties. In particular, this invention provides, among others, compounds generally able to stimulate many members of the protein kinase C family but which lack the inflammatory toxicity of previously known protein kinase C activators. Because protein kinase C activators can, with prolonged exposure, result in the down-regulation of certain protein kinase C isotypes in certain cells, tissues and organs, this invention also provides a means for blocking certain protein kinase C activitities.

DETAILED DESCRIPTION OF THE INVENTION

The invention provides compounds of the general formula (I):

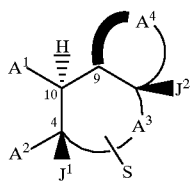

I in the form of an individual isomer, an isomer mixture, a racemate or optical antipode, or a pharmaceutically acceptable salt thereof; wherein $A^1$ and $A^2$ may be individually selected from hydrogen and a straight chain or branched chain, cyclic or acyclic, saturated, unsaturated and/or aromatic carbon- and/or heteroatom-containing substituent having not more than 34 carbon atoms, not more than 24 halogen atoms and not more than 6 heteroatoms selected from oxygen, nitrogen, silicon, phosphorus, boron and sulfur or wherein $A^1$ and $A^2$ taken together complete a 5- or 6-membered carbocyclic or heterocyclic ring, optionally substituted by, respectively, up to six or up to eight straight chain or branched chain, cyclic or acyclic, saturated, unsaturated, and/or aromatic carbon- and/or heteroatom-containing groups, which groups may optionally form one or two additional rings by connection among themselves and/or to $J^1$ or $A^4$ and which taken together contain a total of not more than 30 carbon atoms, not more than 24 halogen atoms and not more than 9 heteroatoms selected from oxygen, nitrogen, silicon, phosphorus, boron and sulfur; wherein $A^3$ is a three atom chain which completes a 7-membered carbocyclic ring optionally substituted by up to six straight chain or branched chain, cyclic or acyclic, saturated, unsaturated, and/or aromatic carbon- and/or heteroatom-containing groups, which groups taken together, excluding S, contain not more than 12 carbon atoms, not more than 8 halogen atoms, and not more than 5 heteroatoms selected from oxygen, nitrogen, silicon, phosphorus and sulfur; provided that, excluding S, the middle carbon atom of $A^3$ is not substituted by hydroxymethyl or 1-hydroxyethyl; wherein $A^4$ completes a 6-membered carbocyclic ring connected in the β configuration to carbon atom 9, optionally substituted by up to eight straight chain or branched chain cyclic or acyclic, saturated, unsaturated and/or aromatic carbon- and/ or heteroatom-containing groups linked to $A^4$ by single or double bonds, the group or groups optionally completing one or two additional rings by themselves and/or one or two additional rings when taken together with $A^1$, $A^2$, a ring formed by $A^1$ and $A^2$ together, and/or a bond to carbon atom 9, which groups taken together include not more than 50 carbon atoms, not more than 24 halogen atoms, and not more than 15 heteroatoms selected from oxygen, nitrogen, silicon, phosphorus, boron and sulfur, and wherein $A^4$ carries at least one substituent other than hydrogen or hydroxyl at carbon 12 and a hydroxy, unsubstituted amino, thiol, hydroxymethyl, mercaptomethyl, aminomethyl, 2-hydroxyethyl, carboxy, unsubstituted carboxamido or unsubstituted aminocarbonyloxy group in the α configuration on carbon 13 or an oxo or thiono group on carbon 13; wherein carbon 9 may be optionally bound to hydrogen or to a substituent selected from hydroxy, acyloxy, orthoesteroxy, ether or silyl ether; wherein $J^1$ is selected from hydrogen, fluoro, chloro, hydroxy, amino, mono- or di(lower-alkyl)amino, methyl, ethyl, vinyl, ethynyl, propargyl, cyano, methoxy, ethoxy, trifluoromethyl, 2-hydroxyethyl, 2-hydroxypropyl, 3-hydroxypropyl, acetoxy, propanoyloxy, acetyl, propanoyl, hydroxyacetyl, 2-hydroxypropanoyloxy, 3-hydroxypropanoyl, acetamido, propanamido, hydroxyacetamido, 2-hydroxypropanamido, or 3-hydroxypropanamido, any of which must be situated in the β configuration, or wherein $J^1$ taken together with $A^1$, $A^2$, or a ring formed by $A^1$ together with $A^2$ completes a 3- to 7-membered substituted or unsubstituted carbocyclic or heterocyclic ring; wherein $J^2$ is selected from hydrogen, methyl, ethyl, hydroxymethyl, hydroxyethyl, vinyl, ethynyl, allyl, propargyl, n-propyl and iso-propyl; and wherein S is bound to carbon 5, 6, or 7 and is selected from hydroxymethyl, 1-hydroxyethyl or 2-hydroxy-2-propyl or from esters or ethers of hydroxymethyl, 1-hydroxyethyl or 2-hydroxy-2-propyl.

The compounds of this invention are further illustrated by the formula $I_R$:

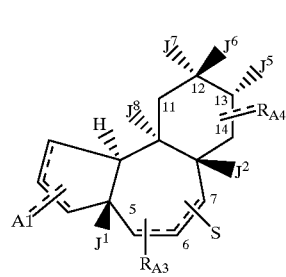

$I_R$ wherein $J^1$, $J^2$ and S are as defined above; and wherein carbons (1 and 2) or (2 and 3) may be joined by a double bond; carbons (5 and 6) or (6 and 7) may be joined by a double bond; S may be bonded to carbon 5, 6 or 7; $R_{A1}$ represents not more than 6 identical or different substituents bonded independently via single and/or double bonds to carbons 1, 2 and/or 3, which substituents may optionally form one or two additional rings by connection among themselves and/or to $J^1$ or the substituents on the 6-membered ring and which may independently be halogen(s) and/or other groups, which halogens and groups taken together contain a total of not more than 30 carbon atoms, not more than 24 halogen atoms and not more than 9 heteroatoms selected from oxygen, nitrogen, silicon, phosphorus and sulfur; $R_{A3}$ represents not more than 6 identical or different substituents bonded independently via single and/or double bonds to carbons 5, 6 and/or 7, which substituents may independently be halogen(s) and/or other groups, which halogens and groups taken together contain not more than 12 carbon atoms, not more than 8 halogen atoms, and not more than 5 heteroatoms selected from oxygen, nitrogen, silicon, phosphorus and sulfur; and $R_{A4}$ represents not more than 8 identical or different substituents bonded independently via single or double bonds to carbons 11, 12, 13 and/or 14, which substituents may independently be halogen(s) and/or other groups, said group or groups optionally completing 1–3 additional rings through bonds among themselves and/or 1–5 additional rings when taken together with the 5-membered ring and/or its substituent(s) $R_{A1}$ and/or $J^8$, and which halogen(s) and groups taken together include not more than 50 carbon atoms, not more than 24 halogen atoms, and not more than 15 heteroatoms selected from oxygen, nitrogen, silicon, phosphorus and sulfur; $J^5$ is a hydroxy, amino, thiol, hydroxymethyl, mercaptomethyl, aminomethyl, 2-hydroxyethyl, carboxy, unsubstituted carboxamido or unsubstituted aminocarbonyloxy group in the α configuration on carbon 13 or is a keto group or thionic keto group doubly bonded to carbon 13; the substituents on carbon 12, $J^6$ and $J^7$, may not both be hydrogen; if either $J^6$ or $J^7$ is hydroxyl, the other may not be hydrogen or hydroxyl; $J^8$ is selected from hydrogen, hydroxy, acyloxy, orthoesteroxy, ether, silyl ether or a bond with $J^4$ to form a ring.

Illustrative examples of compounds of the $I_R$ type include, without limitation, derivatives of crotophorbolone and bisdehydrophorbol,

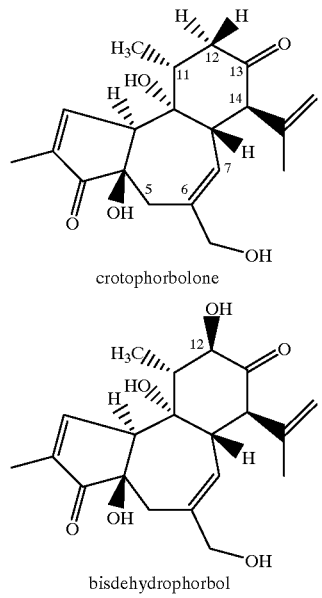

crotophorbolone bisdehydrophorbol such as 12-decyl-15,17-dihydrocrotophorbolone, 12-benzylidene-15,17-dihydrocrotophorbolone, bisdehydrophorbol 12-myristate, 13-deoxo-13-α-hydroxybisdehydrophorbol 12-octyldimethylsilyl ether and 13-deoxo-13-α-carboxybisdehydrophorbol 12-[3',5'-bis(trifluoromethyl)phenyl]carbamate.

It will also be appreciated by those skilled in the pharmaceutical arts that various compounds of the present invention will have different preferred structural features, depending on the intended use of the compounds in question. For example, it has generally been found that adding substituents of moderate hydrophobicity, e.g. substituents carrying hydrocarbon moieties of from about 4 to about 25 carbon atoms, to the A-ring and/or C-ring of diterpene phorboids increases the biological potency of the resulting compounds. Such highly potent compounds might be desired in some therapeutic settings to have a long biological half-life in the patient, while in other therapeutic settings a short half-life might be desired.

To achieve the metabolic stability needed for long biological half-life, for example, substituents bound to the A-ring or C-ring via heteroatom-free carbon linkages or, depending on the organism and tissue involved, the metabolism-resistant heteroatom linkages such as ether, dialkyl- or alkylarylphosphinate and derivatives, carbonate, carbamate, amides of certain types, sterically hindered ester, sulfur-for-oxygen analogs of the foregoing heteroatom linkages, and linkages comprising silyl-carbon bonds, silyl ethers, diradylsulfoxides, diradylsulfones, or amines at the secondary level of alkyl substitution or greater.

On the other hand, selection of A-ring or C-ring substituents with metabolically labile linkages to the A- or C-rings would be preferred when compounds short in vivo half-lives are desired. Examples of such linkages include unhindered esters, phosphodiesters, sulfate diesters and some amides.

Other preferred embodiments of $I_R$ are illustrated by, but not limited to, structures carrying a substituted or unsubstituted cyclopropyl ring, forming $I_P$

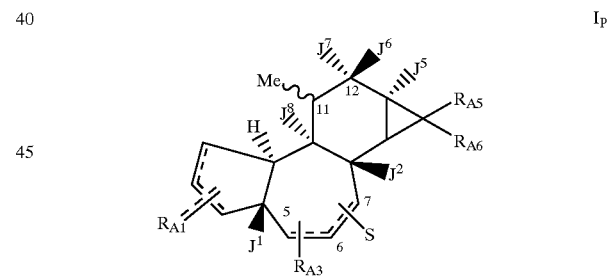

$I_P$ wherein $J^1$, $J^2$, $J^5$, $J^6$, $J^7$, $J^8$, $R_{A1}$, $R_{A3}$ and S are as defined above; and wherein the $R_{A5}$ and $R_{A6}$ radicals may independently be hydrogen, halogen and/or other groups, which halogens and groups taken together contain a total of not more than 30 carbon atoms, not more than 24 halogen atoms and not more than 9 heteroatoms selected from oxygen, nitrogen, silicon, phosphorus and sulfur.

In preferred compounds further illustrating $I_P$, carbon 2 carries a methyl group, $J^1$ is hydroxy, carbon 9 carries a hydroxy group in the α configuration, carbons 10 and 14 carry hydrogens in the a configuration, carbon 11 carries a methyl group in the α configuration and $R_{A5}$ and $R_{A6}$ are both methyl, forming $I_{PP}$:

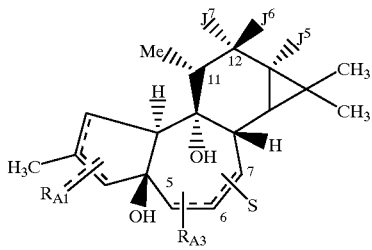

wherein $J^5$, $J^6$, $J^7$, $J^8$, $R_{A1}$, $R_{A3}$ and S are as defined above; and wherein either $J^6$ or $J^7$ is linked to carbon 12 via a carbon atom and the other of $J^6$ or $J^7$ is linked to carbon 12 via an oxygen atom.

In particular, the compound of the formula $I_{PP}$ may be a phorbol 12-ester or a phorbol 12-carbamate. Examples of the formula ($I_{PP}$) are:

phorbol 12-myristate;
phorbol 12-(2',4'-difluorophenylacetate);
phorbol 12-[4'-(9",10'-dihydrophenanthrene-2')butyrate];
phorbol 12-[3',5'-bis(trifluoromethyl)benzoate];
phorbol 12-[3',5'-bis(trifluoromethyl)phenylacetate];
phorbol 12-(4'-n-hexylbenzoate);
phorbol 12-(3',5'-dimethoxyphenylacetate);
phorbol 12-(4'-phenylbenzoate);
phorbol 12-[3',5'-bis(trifluoromethyl)phenylcarbamate];
phorbol 12-n-octadecylcarbamate; and
phorbol 12-(pentafluorophenyl)carbamate.

The invention also includes novel compounds per se having the general formula (I) as hereinbefore defined but excluding bisdehydrophorbol 12-acetate, bisdehydrophorbol 12,20-diacetate, phorbol 12-n-alkanoyl esters, phorbol 12-alkenoyl esters, phorbol 12-(2'-methylbutanoate), phorbol 12-benzoate and phorbol 12-(12'-N-dansylaminodecanoate).

In a further aspect, the invention provides the use of a compound, novel or known, of the formula (I) for the manufacture of a medicament for treating inflammatory conditions.

Also provided is a pharmaceutical composition containing a compound of the formula (I) and a pharmaceutically acceptable carrier. Excluded from this definition are the simple solutions of known diterpene phorboids discussed in the introductory portion of this Specification, for example as disclosed by Schmidt and Hecker (*Carcinogenesis*, Vol. 7, Ed. by E. Hecker et al., Raven Press, New York, 1982, pp 57–63). Thus, simple solutions of the known phorbol 12-esters wherein the carrier is water, dimethylsulfoxide, acetone, or methanol or ethanol of greater than 80% concentration in water, are excluded from the term "pharmaceutical compositions".

The compounds of this invention have been found to possess valuable pharmacological properties for human and veterinary medicine. For therapeutic use in humans or animals the compounds of this invention are dispensed in unit dosage form comprising from about 0.001 to 3000 mg per unit dosage in a pharmaceutically acceptable carrier. In particular, unit dosages in the range of 0.1 to 100 mg are preferred. The compounds of this invention may also be incorporated in topical formulations in concentrations of about 0.001 to 20 weight percent, with concentrations of 0.01 to 10 weight percent being preferred.

It will be appreciated that the actual preferred amounts of active compound in a specific case will vary according to the specific compound being utilized, the particular compositions formulated, the mode of application, and the particular sites and organism being treated. Compounds of this invention having higher potencies should be used in generally smaller amounts, and compounds with lower potencies should be used in generally larger amounts. Dosages for a given host, whether a small animal such as a cat or a human patient, can be determined using conventional considerations, e.g., the host's weight or body surface area. In general, the compounds of the present invention are administered in unit doses of about 0.000015 to about 50 mg/kg of body weight, and quantities of about 0.01 to about 15 mg/kg of body weight are preferred.

As specific examples, representative compounds of this invention variously block inflammation; show cytostatic and/or cytotoxic activity against very diverse types of human cancer cells representative of several human cancers such as leukemia, carcinoma and melanoma; inhibit the infection of human lymphoid cells by HIV; and induce production of thrombolytic activity. These effects are demonstrated by (i) inhibition in the standard topical in vivo mouse ear inflammation model for anti-inflammatory and anti-psoriatic agents wherein inflammation and/or edema by established agonists such as PMA and the ionophore A23187 are blocked; (ii) by the inhibition of proliferation of human leukemic cells in culture via induction of differentiation; (iii) by assays of cytotoxicity against human carcinoma cancer cells; (iv) by assays of inhibition of growth of human melanoma cells; (v) by assays of inhibitory activity against HIV viral replication in human lymphocyte cells; and (vi) by measurement of stimulation of fibrinolytic activity in cultured cells. These demonstrations of efficacy are achieved at doses per ear, per kg of body weight or per kg of bodily fluid equivalent, using representative compounds of the present invention, as follows: (i) about 0.01–1000 nanogram/ear, corresponding to about 0.0001–10 mg per square meter of body surface being treated; (ii) about 0.1–100 mg/kg fluids; (iii) about 0.1–100 mg/kg fluids; (iv) about 1–100 mg per kg of fluids; (v) about 0.1–100 mg/kg fluids; and (vi) about 0.1–100 mg/kg fluids, respectively.

The activities of representative compounds of this invention against the three diverse types of human cancer cells described above are particularly noteworthy. Cancer is in fact a broad classification containing at least 110 clinically different types of neoplastic diseases. The activities of compounds of this invention against three very different types of cancer cells demonstrate not only their utilities against specific human cancer cells but also the significant breadth for the anti-cancer effects of this invention beyond a single class of cancer disease, indicative of additional anti-cancer utilities.

The anti-viral activities of compounds of this invention are also of great importance. For example, the tests demonstrating the anti-HIV properties of these compounds [see Example 8] were carried out in widely validated and accepted cellular assays of HIV infectivity in human cells that are indicative of in vivo activity. Thus the anti-HIV properties of the compounds of this invention relate directly to the in vivo activities of standard anti-HIV reverse transcription inhibitors such as azidothymidine, dideoxyinosine, dideoxycytidine and non-nucleoside reverse transcription inhibitors, HIV-protease inhibitors and inhibitors of tat-gene function, which are fully active in the anti-HIV assay by which the compounds of this invention were tested. This is in contrast to many in vitro HIV-related assays that are unable to provide predictive information about the anti-HIV effects of test compounds in living cells, such as assays of inhibition against isolated HIV enzymes. For example, the inadequacy of isolated enzyme assays was indicated by the finding that, of two compounds able to inhibit the HIV protease when assayed on the purified protease enzyme, only one of the compounds was able to inhibit HIV infectivity in the whole-cell assay in human lymphocytes [T. K. Antonucci et al., "Characterizations of HIV-1 protease inhibitors" in *Innovations in therapy of human viral diseases: Wellcome Symposium*, Dec. 6–9, 1992, Book of Abstracts, Page 2.]

The compounds of this invention also show selective effects as antagonists for protein kinase C in some cases, as noninflammatory agonists for protein kinase C in other cases, and as selective ligands for protein kinase C and/or for phorboid receptors.

Thus, compounds of the present invention can be used as agents for the abrogation of pathophysiological conditions and disease states in applications such as anti-inflammatory, anti-psoriatic, anti-cancer, anti-ulcer, anti-hypertensive, anti-asthma, anti-arthritic, anti-autoimmune, anti-nociceptive, anti-secretory, anti-parasitic, anti-amoebic, anti-viral including anti-HIV replication, anti-Alzheimer's disease, in prophylaxis against infection by any HIV form, and any other application in which pathological involvement of protein kinase C is found.

As an example of the numerous diseases for which extensive literature data are available to demonstrate a role of PKC as a therapeutic target, the connection between PKC and anti-viral indications provides a general model of such analysis. Evidence for involvement of protein kinase C in the physiology of many human and animal pathogenic viruses has long been known, particularly from experiments in which a standard protein kinase C activator such as a phorbol ester greatly stimulates viral production for many different kinds of viruses [see, for example: H. zur Hausen et al., "Persisting oncogenic herpesvirus induced by the tumour promoter TPA", *Nature* 272: 373–375 (1978); H. zur Hausen et al., "Tumor initiators and promoters in the induction of Epstein-Barr virus", *Proc. Natl. Acad. Sci. USA* 76: 782–785 (1979); D. V. Ablashi et al., "Increased infectivity of oncogenic Herpes viruses of primates with tumor promoter 12-O-tetradecanoylphorbol-13-acetate", *Proc. Soc. Exp. Biol. Med.* 164: 485–490 (1980); G. Colletta et al., "Enhancement of viral gene expression in Friend erythroleukemia cells by 12-O-tetradecanoylphorbol-13-acetate", *Cancer Research* 40: 3369–3373 (1980); S. K. Arya, "Phorbol ester-mediated stimulation of the synthesis of mouse mammary tumour virus", *Nature* 284: 71–72 (1980); K. B. Hellman and A. Hellman, "Induction of type-C retrovirus by the tumor promoter TPA", *Int. J. Cancer* 27: 95–99 (1981); E. Amtmann and G. Sauer, "Activation of non-expressed bovine papilloma virus genomes by tumour promoters", *Nature* 296: 675–677 (1982); L. S. Kucera, et al., "12-O-Tetradecanoyl-phorbol-13-acetate enhancement of the tumorigenic potential of Herpes Simplex virus type 2 Transformed cells", *Oncology* 40: 357–362 (1983); and V. Wunderlich et al., "Enhancement of primate retrovirus synthesis of tumor promoters", Symposium on role of cocarcinogens and promoters in human and experimental carcinogenesis, May 16–18, 1983, Budapest, Hungary, *Book of Abstracts*, p. 88].

Similar experiments indicate involvement of protein kinase C in the life cycle of HIV, and initial molecular genetics studies helped illuminate the mechanisms by which cellular protein kinase C can influence HIV [see, for example: S. Harada et al., "Tumor promoter, TPA, enhances replication of HTLV-III/LAV", *Virology* 154: 249–258 (1986); H. Dinter et al., "In Vitro activation of the HIV-1 enhancer in extracts from cells treated with a phorbol ester tumor promoter", *EMBO Journal* 6: 4067–4071 (1987); J. D. Kaufman et al., "Phorbol ester enhances human immunodeficiency virus-promoted gene expression and acts on a repeated 10-base-pair functional enhancer element", *Mol. Cell. Biol.* 7: 3759–3766 (1987); and M. Siekevitz et al., "Activation of the HIV-1 LTR by T cell mitogens and the transactivator protein of HTLV-I", *Science* 238: 1575–1578 (1987)].

These and later molecular genetics-based virological investigations provided clear mechanistic explanations for the effects, observed much earlier, of protein kinase C modulators on the life cycles of numerous human and animal viruses. Such studies showed that many viruses contain genetic control elements, called enhancers, whose functions in controlling viral expression involve the protein kinase C of the host cell. Of particular importance for the role of protein kinase C in virus-cell interactions are the enhancers known as AP-1 and NF-κB [see, for example: J. E. Marich et al., "The phylogenetic relationship and complete nucleotide sequence of human papillomavirus Type 35", *Virology*: 770–776 (1992); R. L. Smith et al., "Activation of second-messenger pathways rectivates latent Herpes Simplex virus in neuronal cultures", *Virology* 188: 311–318 (1992); S. L. Gdovin and J. E. Clements, "Molecular mechanisms of visna virus tat: identification of the targets for transcriptional activation and evidence for a post-transcriptional effect", *Virology* 188: 438–450 (1992); D. S. Shih et al., "Involvement of FOS and JUN in the activation of visna virus gene expression in macrophages through an AP-1 site in the viral LTR", *Virology* 190: 84–91 (1992); A. Mirza, "Stimulation of adenovirus early gene expression by phorbol ester: its possible mechanism", *Virology* 190: 645–653 (1992); E. J. Wade et al., "An AP-1 binding site is the predominant cis-acting regulatory element in the 1.2-kilobase early RNA promoter of human cytomegalovirus", *J. Virology* 66: 2407–2417 (1992); F. Stubenrauch et al., "Late promoter of human papillomavirus Type 8 and its regulation", *J. Virology* 66: 3485–3493 (1992); F. Thierry et al., "Two AP-1 sites binding JunB are essential for human papillomavirus Type 18 transcription in keratinocytes", *J. Virology* 66: 3740–3748 (1992); J. Liu et al., "Specific NF-κB subunits act in concert with tat to stimulate human immunodeficiency virus Type 1 transcription", *J. Virology* 66: 3883–3887 (1992); W. A. Jensen et al., "Inhibition of protein kinase C results in decreased expression of bovine leukemia virus", *J. Virology* 66: 4427–4433 (1992); K. Shiroki et al., "Adenovirus E1A proteins stimulate inositol phospholipid metabolism in PC12 cells", *J. Virology* 66: 6093–6098 (1992); J. C. Cross et al., "Transactivation by hepatitis B virus X protein is promiscuous and dependent on mitogen-activated cellular serine-threonine kinases", *Proc. Natl. Acad. Sci. USA* 90: 8078–8082 (1993); and A. S. Kekule et al., "Hepatitis B virus transactivator HBx uses a tumour promoter signalling pathway", *Nature* 361: 742–745 (1993)].

The compounds of this invention can also be used in combination with other therapeutic agents, for example for use in the treatment of viral infections. Thus, a compound of this invention can be used in combination with a nucleoside analog such as azidothymidine or dideoxyinosine, a tetrahydroimidazo[4,5,1jk][1,4]-benzodiazepin-2(1H)-one derivative, other HIV reverse transcriptase inhibitors, HIV protease inhibitors, or HIV tat-gene function inhibitors for the prophylaxis against or treatment of HIV infections. A method for treating a mammal infected with a virus comprises administering to a mammal in need of such treatment an antivirally effective quantity of a composition comprising an acceptable pharmaceutical carrier and an antivirally active compound or compounds or a pharmaceutically acceptable salt thereof.

Furthermore, the compounds of this invention may be used to achieve desired physiological results such as interferon release, interleukin induction, tumor necrosis factor production, immune system stimulation and/or reconstitution, insulin secretion, insulinomimetic activity, acceleration of wound healing, improvement in central nervous system functions such as memory and learning and abrogation of the symptoms or progress of Alzheimer's disease, and any other application for which desirable actions of protein kinase C are found.

As phorboid receptor subtype- and/or protein kinase C subtype-selective ligands, the compounds of this invention also have very valuable application as experimental agents for research into the role of protein kinase C and/or phorboid receptors in important biological processes and in human and veterinary diseases. Thus, their value extends to their use as pharmacological tools for in vitro and in vivo research, in a manner similar to the important roles that selective agonists and antagonists have played in the studies of the mechanism of action of adrenergic, dopaminergic, opiate, benzodiazepine, cholinergic, and serotoninergic receptor systems, among others.

In addition, the compounds can be used in in vitro diagnostics (e.g., in an assay for protein kinase C). They are also useful as intermediates in the production of other drugs, e.g., as described in the present invention.

The compounds of this invention are generally administered to animals, including but not limited to fish, avians, and mammals including humans.

The pharmacologically active compounds of this invention can be processed in accordance with conventional methods of galenic pharmacy to produce medicinal agents for administration to patients, e.g., mammals including humans.

The compounds of this invention can be employed in admixture with conventional excipients and carriers, i.e., pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcoholics, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., enzyme inhibitors, to reduce metabolic degradation. Such carriers do not include the following solvents when used alone: water, dimethylsulfoxide, acetone, or methanol or ethanol of greater than 80% concentration in water.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules. A syrup, elixir, or the like can be used wherein a sweetened vehicle is employed.

A preferred method of administration comprises oral dosing, with tablets, dragees, liquids, drops, or capsules. For the oral route of administration, either compounds of this invention lacking functional groups destroyed by acid, or tablets or capsules which protect the active compound from upper gastrointestinal acidity, are preferred.

Sustained or directed release compositions can be formulated, e.g., in liposomes or in compositions wherein the active compound is protected with differentially degradable coatings, e.g., by microencapsulation, multiple coatings, absorption onto charcoal, entrapment in human serum albumin microspheres, etc. It is also possible to freeze-dry the new compounds and use the lyophilizates obtained, for example, for the preparation of products for injection.

Another preferred route of administration comprises topical application, for which are employed nonsprayable forms, viscous to semi-solid or solid forms comprising a carrier compatible with topical application and having a dynamic viscosity compatible with topical application, preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

The compounds of this invention, admixed with appropriate carriers, may also be delivered to subjects by means of an externally connected or internally implanted pumping device to give a controlled and/or sustained release of the therapeutic mixture, or by means of a patch of natural or synthetic fabric and/or polymer impregnated with the compounds in a suitable carrier and affixed to the skin to achieve transdermal release and absorption of the active compounds.

The compounds of this invention may also be modified by covalent attachment of metabolically modifiable groups, to form "prodrugs" which are released by cleavage in vivo of the metabolically removable groups. For example, amine, hydroxy and/or thiol groups present in many compounds of this invention may be converted to prodrugs by covalent attachment of acyl or aminoacyl organic functional groups. Likewise, compounds of this invention containing carboxylic, sulfonic, phosphoric, phosphonic or related free acids, including those in which one or more oxygen atoms are replaced by sulfur, may be converted to prodrugs by formation of their esters or amides by covalent attachment of alcohols, amines, amino acids and the like. Compounds of this invention may also incorporate N-alkyldihydropyridine functional groups, which become localized to the central nervous system after administration to the subject and subsequent metabolic modification of the N-alkyldihydropyridine group in the central nervous system.

It will be recognized by persons with ordinary skill in medicinal chemistry that conversion of alcohol-, amine-, thiol- or acid-containing compounds of this invention to prodrugs is preferably done by derivatization of such groups located in regions of the molecule having minimal steric hindrance, to permit access of metabolizing enzymes, other bioreactants or water.

It will be appreciated that starting materials for obtaining compounds of this invention from natural sources or from total or partial synthesis may be altered in very diverse ways, consistent with this invention, to obtain compounds with novel and diverse primary biological/medicinal activities resulting from, and controlled by, the polar group attached to carbon 13; such properties include, for example, loss of skin inflammatory activity and appearance or retention of anti-inflammatory, anti-HIV, anti-leukemic and cytokine-induction activities. It is also possible to introduce an extremely wide variety of changes into the parent structure and its substituents permitted in the present invention, especially the substituent at carbon 12, to obtain new entities with improved secondary properties, such as, variously, hydrophobicity, water solubility, high potency, oral availability, metabolic and chemical stability or lability as desired, reduced therapeutic side effects, and so on, using strategies and techniques widely recognized in the art of medicinal chemistry and pharmacology.

Starting materials for the synthesis of the compounds of this invention may be obtained from any of a wide variety of natural sources and by total synthesis. Notable among the abundantly available natural starting materials are phorbol, bisdehydrophorbol and crotophorbolone, which have long been known in the literature and art of phorboid chemistry [see e.g. Hecker, E. and Schmidt, R., *Fortschritte der Chemie Organischer Naturstoffe* 31: 377–467 (1974), Thielmann, H.-W. and Hecker, E., *Liebigs Ann. Chem.* 728: 158–183 (1969) and *Naturally Occurring Phorbol Esters,* ed. F. J. Evans, CRC Press, Boca Raton (1986), chapters 7, 8 and 9 and references cited therein].

Furthermore, the diterpene phorboids of this invention are available by total synthesis from common organic chemical starting materials. These syntheses provide a variety of approaches and associated flexibility in arriving at widely diverse functionalities on the parent nucleus [see Paquette, L. et al., *J. Am. Chem. Soc.* 106: 1446–1454 (1984); Rigby, J. and Moore, T., *J. Org. Chem.* 55: 2959–2962 (1990); Wender, P. et al., *J. Am. Chem. Soc.* 111: 8954–8957 (1989); Wender, P. et al, *J. Am. Chem. Soc.* 111: 8957–8958 (1989); and Wender, P. and McDonald, F., *J. Am. Chem. Soc.* 112: 4956–4958 (1990)].

The means for modifying the diterpenoid phorboids to produce the compounds of this invention will be obvious to workers with ordinary skill in synthetic organic chemistry.

Using naturally occurring parent compounds, routine synthetic routes, transformations and procedures common in the art of synthetic organic chemistry and extensively exemplified in, for example, Hecker and Schmidt, op.cit. and in Thielmann and Hecker, op.cit., are sufficient for highly varied and extensive practice of this invention. Compounds of this invention may be obtained by semisynthetic procedures, starting from any of a variety of compounds from naturally occurring sources, using very routine synthetic strategies to protect sensitive hydroxy and keto groups at, for example, the 3, 4, 9 and/or 20 positions of the diterpenes (phorbol numbering) during subsequent steps aimed at modifying the C-ring.

Frequently one or more oxygen atoms must be blocked before some types of chemical modifications may be accomplished on the other portions of the diterpene parents available easily from natural sources. Many widely used and thoroughly characterized protecting groups for the oxygen atoms present as hydroxy groups are acyl, benzyl, trialkylsilane, benzyloxycarbonyl, 4'-methoxyphenyldiphenylmethyl and trimethylsilylyethoxycarbonyl, which are variously stable to or removed under acidic, basic or reducing conditions or with fluoride ion reagents. Carbonyl functions may be protected by conversion to acetals or ketals, or by reduction to the alcohol level followed by protection with standard protecting groups for the hydroxy group.

C-ring modifications in suitably protected crotophorbolone and bisdehydrophorbol compounds, for example, can include a wide range of very routine manipulations of keto and hydroxy groups, including oxidation, reduction, alkylation, esterification, etherification, formation of carbamates, etc.

Standard techniques for removal of protecting groups then provide any of a very diverse selection of agents having the particular features taught in this invention, particularlyl with respect to the substitution patterns on carbons 12 and 13. The use and removal of such groups is obvious and accessible to any worker with modest skill in the art of synthetic organic chemistry without undue experimentation.

The use of the methods of total synthesis as described in the literature cited above permits specific modifications of the parent structures of the diterpenoids. By established techniques in the art of organic synthesis modified parent structures may be obtained which embody alterations at any of the numerous permitted substituent locations and which have useful biological activity as taught by the present invention. This wide variety of modified diterpenoid structures may result from the use of modified starting materials, from modifications of one or more synthetic steps or from a combination of both, as applied to the examples in the synthetic organic and natural product literature cited above by workers of ordinary skill in synthetic organic chemistry.

This invention is illustrated further by the following examples.

EXAMPLE 1

Phorbol 12-[4'-(9",10"-Dihydrophenanthrene-2") butyrate]

A solution of 2.95 g of 4-(9',10'-dihydrophenanthrene-2') butyric acid and 1.13 g of dicyclohexylcarbodiimide in 20 mL of tetrahydrofuran was warmed briefly with a hot air gun and then stirred for 5 min at room temperature. The mixture was then filtered and concentrated in vacuo to obtain 2.79 g of the 4-(9',10'-dihydrophenanthrene-2')butyric anhydride. This anhydride was mixed with 1.6 g of 20-O-[diphenyl-(4'-methoxyphenyl)methyl]phorbol 13-O-isopropyldimethylsilyl and then 15 mL of pyridine was added. After 18 h of stirring under nitrogen 100 mg of 4-dimethylaminopyridine was added followed 7 h later with 400 mg of dicyclohexylcarbodiimide. After another 22 h at room temperature approximately 10 mL of methanol was added followed by the concentration of the mixture in vacuo. The residue was partitioned between ethyl acetate and phosphate buffer (pH 2) and the organic layer washed with phosphate buffer (pH 8), filtered through a sintered glass funnel containing silica, sodium sulfate and sodium chloride ("N/N/S") and again concentrated in vacuo. Purification by preparative liquid chromatography [silica; hexane/ethyl acetate (75:25)] afforded slightly impure 20-O-[diphenyl-(4'-methoxyphenyl)methyl]phorbol 12-[4'-(9",10"-dihydrophenanthrene-2")butyrate] 13-O-isopropyldimethylsilyl.

The entire sample of the above compound was dissolved in 35 mL of t-butylmethyl ether and treated with 150 mL of 90% acetic acid in water. After 70 min the mixture was concentrated in vacuo and partitioned between ethyl acetate and phosphate buffer (pH 8) followed by concentration of the organic layer in vacuo. Preparative liquid chromatography [silica; methylene chloride/methanol (97:3)] afforded 890 mg of phorbol 12-[4'-(9",10"-dihydrophenanthrene-2") butyrate].

EXAMPLE 2

In a manner similar to Example 1, utilizing standard protection and deprotection procedures for hydroxy groups, the following compounds are made:

i) phorbol 12-(2',4'-difluorophenylacetate);

ii) 3-deoxo-3-beta-hydroxyphorbol 12-[4'-(9",10"-dihydrophenanthren-2")butyrate];

iii) phorbol 12-[3',5'-bis(trifluoromethyl)benzoate];

iv) phorbol 12-[3',5'-bis(trifluoromethyl)phenylacetate];

v) phorbol 12-(4'-n-hexylbenzoate);

vi) phorbol 12-(3',5'-dimethoxyphenylacetate);

vii) phorbol 12-(4'-phenylbenzoate);

viii) 12-alpha-phorbol 12-(4'-n-hexylbenzoate);

ix) phorbol 12-(pentafluorophenyl)acetate; and x) bisdehydrophorbol 12-myristate.

EXAMPLE 3

20-O-[Diphenyl(4'-methoxyphenyl)methyl]phorbol 12-[3',5'-Bis(trifluoromethyl)phenylcarbamate] 13-Methoxyacetate To a solution of 396 mg of 20-O-[diphenyl(4'-methoxyphenyl)methyl]phorbol 13-methoxyacetate, 70 mg of 4-dimethylaminopyridine and 72 mg of dibutyltin dilaurate in 5 mL of tetrahydrofuran was added 220 mg of 3,5-bis(trifluoromethyl)phenyl isocyanate in 1 mL tetrahydrofuran. After 7 h another 100 mg of the isocyanate was added. After stirring for another 12 h at room temperature the reaction mixture was partitioned between ethyl acetate/hexane and water. The organic layer was filtered through N/N/S and concentrated in vacuo to afford 872 mg of crude 20-O-[diphenyl-(4'-methoxyphenyl)methyl]phorbol 12-[3',5'-bis(trifluoromethyl)phenylcarbamate] 13-methoxyacetate.

EXAMPLE 4

In a manner similar to the methods of Example 3 the following compounds are prepared:

(i) 20-O-[diphenyl(4'-methoxyphenyl)methyl]phorbol 12-n-octadecylcarbamate 13-methoxyacetate; and (ii) 20-O-[diphenyl(4'-methoxyphenyl)methyl]phorbol 12-(pentafluorophenyl)carbamate 13-methoxyacetate.

EXAMPLE 5

Phorbol 12-[3',5'-Bis(trifluoromethyl) phenylcarbamate]

To a solution of 174 mg of 20-O-[diphenyl(4'-methoxyphenyl)methyl]phorbol 12-[3',5'-bis (trifluoromethyl)phenylcarbamate] 13-methoxyacetate in 5 mL of methanol was added approximately 20 mg of sodium carbonate. After 4.5 h the mixture was partitioned between water and ethyl acetate. The organic layer was filtered through N/N/S and concentrated in vacuo. The resulting residue was dissolved in 2.7 mL dry methylene chloride and 0.7 mL of absolute ethanol and treated with 0.05 mL of trifluoroacetic acid. After 1.5 h the mixture was partitioned between ethyl acetate and phosphate buffer (pH 8). The organic layer was filtered through N/N/S and concentrated in vacuo. Preparative liquid chromatography [silica; hexane/ethyl acetate (50:50)] afforded 27 mg of phorbol 12-[3',5'-bis(trifluoromethyl)phenylcarbamate]. The structure was confirmed by NMR and high resolution mass spectral analysis.

EXAMPLE 6

In a manner similar to the methods of Examples 3–5 the following compounds are prepared:

(i) phorbol 12-n-octadecylcarbamate;

(ii) phorbol 12-(pentafluorophenyl)carbamate;

(iii) bisdehydrophorbol 12-(3',5'-dimethoxybenzyl) carbamate; and (iv) bisdehydrophorbol 12-octylcarbonate.

EXAMPLE 7

Demonstration of Anti-inflammatory Activity

A stock solution of 300 pmoles of the standard inflammatory compound phorbol 12-myristate 13-acetate per 5 $\mu$L acetone was prepared. This solution was used to prepare four-fold dilutions of the agent to be tested, covering concentrations of the latter typically selected from a range of about 4.0 to about 1,200,000 pmoles per 5 $\mu$L. These solutions were used to demonstrate the anti-inflammatory activity of the test compound by application of 5 $\mu$L to the insides of the ears of mice (one ear per mouse), followed by the observation of ear inflammation/erythema at intervals from 1 to 48 hours after application.

In this manner, the anti-inflammatory activities of the following compounds are demonstrated; lower doses produce shorter periods of inflammation/erythema and higher doses produce complete, inhibition during the entire assay period.

(i) phorbol 12-[4'-(9",10"-dihydrophenanthrene-2") butyrate]; and (ii) phorbol 12-(pentafluorophenyl)acetate.

EXAMPLE 8

Demonstration of Anti-HIV Activity

Human peripheral blood lymphocytes were isolated from the buffy coat fractions of blood donations. The lymphocytes were then stimulated with 5 micrograms/ml of phytohemagglutinin for 48 hours. Prior to infection with HIV, the lymphocytes were washed and resuspended in mitogen-free medium. On day 0 the cells were infected with HIV and were cultured for four days in the presence or absence of graded concentrations of the test agent. On days 3 and 4 the supernatant levels of total viral RNA and viral core protein p24 were determined at each drug concentration and dose-response curves were used to determine the concentration of drug giving 50% inhibition of production of viral RNA and of p24 core protein.

Using this method, the anti-HIV $ED_{50}$ value for RNA [drug concentration is in brackets] for the following compound was determined from dose-response curves or by estimation from one or more experimental drug concentrations:

(i) phorbol 12-[4'-(9",10"-dihydrophenanthrene-2") butyrate] [450 nM].

EXAMPLE 9

Demonstration of Anti-melanoma Activity

Human RPMI-7272 melanoma cells were grown in the standard culture medium under normal incubation conditions. On day 1 the cells were cultured in the absence (control) or presence of graded concentrations of the test agent in separate tubes. On day 4 after 72 h of exposure the number of cells in each tube was measured and the number of cell doublings determined. The drug treated tubes were compared to the control tube to arrive at the $ID_{50}$ (the concentration of drug required to inhibit cell doublings by 50%) for the test agent.

By this procedure the anti-melanoma activity of phorbol 12-[4'-(9",10"-dihydrophenanthrene-2")butyrate] was determined, showing an $ID_{50}$ of 12 μM.

EXAMPLE 10

Demonstration of Anti-leukemic Activity

HL-60 promyelocytic leukemia cells were cultured in RPMI 1640 medium supplemented with 10% fetal bovine serum. Cells (7,500) were seeded into 96-well microtiter plates and incubated overnight. Serial dilutions of the test agent (dissolved in DMSO and then diluted with culture medium) were added to the wells on day 1. The plates were incubated for 8 days to allow the control cultures to undergo at least 3 cell divisions. The cell growth was monitored by using the calorimetric MTT (tetrazolium) assay [Mosmann, T., *J. Immunol. Meth.* 65: 55–63 (1983)]. After the incubation period, the cells were washed with phosphate-buffered saline in the microtiter plate. DMSO was then added to each well and the dish was put on a shaker for 20 min. The optical density was measured at 540 nm and compared using the formula: (OD Test–OD Start)/(OD Control–OD Start)×100. The $IC_{50}$ was defined as the drug concentration which leads to 50% of cells per well compared to control cultures (100%) at the end of the incubation period.

By this method the anti-leukemic activities of the following other compounds were demonstrated:

(i) phorbol 12-(pentafluorophenyl)acetate ($IC_{50}$=50.8 μM); and (ii) phorbol 12-[4'-(9",10"-dihydrophenanthrene-2") butyrate] ($IC_{50}$=1.8 μM).

EXAMPLE 11

Demonstration of Anti-cancer Activity

T-24 human bladder carcinoma cells were cultured in Eagle's minimal essential medium supplemented with 5% fetal bovine serum. Cells (1,000) were seeded into 96-well microtiter plates and incubated overnight. Serial dilutions of the test agent (dissolved in DMSO and then diluted with culture medium) were added to the wells on day 1. The plates were incubated for 5–6 days to allow the control cultures to undergo at least 3 cell divisions. After the incubation period, the cells were fixed with glutaraldehyde, washed with water and stained with 0.05% methylene blue. After washing the dye was eluted with 3% HCl. The optical density per well was measured at 665 nm and compared using the formula: (OD Test–OD Start)/(OD Control–OD Start)×100. The $IC_{50}$ was defined as the drug concentration which leads to 50% of cells per well compared to control cultures (100%) at the end of the incubation period.

By this method the anti-cancer activity of the following compound was demonstrated:

(i) phorbol 12-[4'-(9",10"-dihydrophenanthrene-2") butyrate] ($IC_{50}$=4.0 μM).

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound of the formula I:

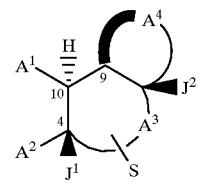

in the form of an individual isomer, an isomer mixture, a racemate or optical antipode, or a pharmaceutically acceptable salt thereof;

wherein $A^1$ and $A^2$ may independently be selected from the group consisting of hydrogen, halogen and a straight chain or branched chain, cyclic or acyclic, saturated or unsaturated or aromatic carbon- and/or heteroatom-containing group having not more than 34 carbon atoms, not more than 24 halogen atoms and not more than 6 heteroatoms selected from the group consisting of oxygen, nitrogen, silicon, phosphorus, boron and sulfur; or, $A^1$ and $A^2$ taken together may complete a 5- or 6-membered carbocyclic or heterocyclic ring, optionally substituted by, respectively, up to six or up to eight straight chain or branched chain, cyclic or acyclic, saturated or unsaturated or aromatic carbon- and/or heteroatom-containing groups, which groups may optionally form one or two additional rings by connection among themselves and/or to $J^1$ or $A^4$ and which, taken together, contain a total of not more than 30 carbon atoms, not more than 24 halogen atoms and not more than 9 heteroatoms selected from the group consisting of oxygen, nitrogen, silicon, phosphorus, boron and sulfur;

$A^3$ is a three atom chain which carries S and completes a 7-membered carbocyclic ring substituted by 0–5 straight chain or branched chain, cyclic or acyclic, saturated or unsaturated or aromatic carbon- and/or heteroatom-containing groups, which, taken together, excluding S, contain not more than 12 carbon atoms, not more than 8 halogen atoms, and not more than 5 heteroatoms selected from the group consisting of oxygen, nitrogen, silicon, phosphorus and sulfur; provided that, excluding S, the middle carbon atom of $A^3$ is not substituted by hydroxymethyl or 1-hydroxyethyl;

$A^4$ completes a 6-membered carbocyclic ring connected in the β configuration to carbon atom 9, substituted by 0–8 straight chain or branched chain, cyclic or acyclic, saturated or unsaturated or aromatic carbon- and/or heteroatom-containing groups, linked to $A^4$ by single or double bonds, the group or groups optionally completing 1–2 additional rings by connections among themselves and/or 1–2 additional rings by connections to $A^1$, $A^2$, a ring formed by $A^1$ and $A^2$ together, and/or a bond to carbon 9, wherein said groups, taken together, include not more than 50 carbon atoms, not more than 24 halogen atoms, and not more than 15 heteroatoms selected from the group consisting of oxygen, nitrogen, silicon, phosphorus, boron and sulfur; and wherein $A^4$ carries at least one substituent which is not hydrogen and is not an hydroxyl at carbon 12 and carries a substituent selected from the group consisting of hydroxy, unsubstituted amino, thiol, hydroxymethyl, mercaptomethyl, aminomethyl, 2-hydroxyethyl, carboxy, unsubstituted carboxamido, unsubstituted aminocarbonyloxy group, each in the α configuration on carbon 13, and an oxo or thiono group on carbon 13;

carbon atom 9 is bound to a moiety selected from the group consisting of hydrogen, hydroxy, acyloxy, orthoesteroxy, ether, silyl ether and a group attached to $A^4$;

$J^1$ may be selected from the group consisting of hydrogen, fluoro, chloro, hydroxy, amino, mono- or di(loweralkyl)amino, methyl, ethyl, vinyl, ethynyl, propargyl, cyano, methoxy, ethoxy, trifluoromethyl, 2-hydroxyethyl, 2-hydroxypropyl, 3-hydroxypropyl, acetoxy, propanoyloxy, acetyl, propanoyl, hydroxyacetyl, 2-hydroxypropanoyloxy, 3-hydroxypropanoyl, acetamido, propanamido, hydroxyacetamido, 2-hydroxypropanamido and 3-hydroxypropanamido each of which must be situated in the β configuration, or $J^1$ taken together with $A^1$, $A^2$, or a ring formed by $A^1$ together with $A^2$ may complete a 3- to 7-membered substituted or unsubstituted carbocyclic or heterocyclic ring, the substituents of which contain not more than 15 carbon atoms, not more than 10 halogens, and not more than 8 heteroatoms selected from the group consisting of oxygen, nitrogen, silicon, phosphorus, boron and sulfur;

$J^2$ is selected from the group consisting of hydrogen, methyl, ethyl, hydroxymethyl, hydroxyethyl, vinyl, ethynyl, allyl, propargyl, n-propyl and isopropyl; and S is bound to carbon 6 and is selected from the group consisting of hydroxymethyl, 1-hydroxyethyl and 2-hydroxy-2-propyl;

provided that: said compound is not: a 12-n-alkanoyl ester, a 12-alkenoyl ester, a 12-(2'-methylbutanoate), 12-benzoate or a 12-(2'-methylamino)benzoate of a compound having the 20-carbon tigliane skeleton; phorbol 12-(12'-N-dansylaminododecanoate); 12-O-methylphorbol; 12-O-ethylphorbol; neophorbol; 12-deoxy-12-oxophorbol; 2-(benzoyloxy)-1,2,3,4,4a,4b,5a,6,6a,7,9a,9b-dodecahydro-3,6,6a,9b-tetrahydroxy-5a-(hydroxymethyl)-1,8-dimethyl-3-(1-methylethenyl)benz[7,8]azuleno[5,6-b]oxiren-4-yl ester of 2,4-decadienoic acid; tiglophorbol B; tiglophorbol; bisdehydrophorbol 12-acetate; or, bisdehydrophorbol 12-tetradecanoate.

2. A compound of claim 1 wherein formula I is $I_R$:

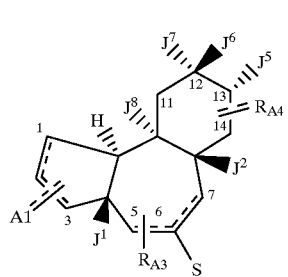

$I_R$ wherein carbons 1 and 2 or carbons 2 and 3 may be joined by a double bond;

carbons 5 and 6 or carbons 6 and 7 may be joined by a double bond;

$R_{A1}$ represents not more than 6 identical or different substituents bonded independently via single and/or double bonds to carbons 1, 2 and/or 3, which substituents may optionally form one or two additional rings by connection among themselves and/or to $J^1$ or substituents on the 6-membered ring and which may independently be selected from the group consisting of hydrogen, halogen and straight chain or branched chain, cyclic or acyclic, saturated or unsaturated or aromatic carbon- and/or heteroatom-containing groups, which, taken together, contain a total of not more than 30 carbon atoms, not more than 24 halogen atoms and not more than 9 heteroatoms selected from the group consisting of oxygen, nitrogen, silicon, phosphorus and sulfur;

$R_{A3}$ represents not more than 5 identical or different substituents bonded independently via single and/or double bonds to carbons 5, 6 and/or 7, which substituents are independently selected from the group consisting of hydrogen, halogen and straight chain or branched chain, cyclic or acyclic, saturated or unsaturated or aromatic carbon- and/or heteroatom-containing groups, which, taken together, contain not more than 12 carbon atoms, not more than 8 halogen atoms, and not more than 5 heteroatoms selected from the group consisting of oxygen, nitrogen, silicon, phosphorus and sulfur;

$R_{A4}$ represents not more than 5 identical or different substituents bonded independently via single or double bonds to carbons 11, 12, 13 and/or 14, which substituents may independently be selected from the group consisting of hydrogen, halogen and straight chain or branched chain, cyclic or acyclic, saturated or unsaturated or aromatic carbon- and/or heteroatom-containing groups, said group or groups optionally completing 1–3 additional rings through bonds among themselves and/or 1–5 additional rings when taken together with the 5-membered ring and/or its substituent(s) $R_{A1}$ and/or $J^8$, and which halogen(s) and groups, taken together, include not more than 50 carbon atoms, not more than 24 halogen atoms, and not more than 15 heteroatoms selected from the group consisting of oxygen, nitrogen, silicon, phosphorus and sulfur;

$J^5$ is selected from the group consisting of hydroxy, amino, thiol, hydroxymethyl, mercaptomethyl, aminomethyl, 2-hydroxyethyl, carboxy, unsubstituted carboxamido, unsubstituted aminocarbonyloxy groups, each in the α configuration on carbon 13, and an oxo or thiono group doubly bonded to carbon 13;

the substituents on carbon 12, $J^6$ and $J^7$, may have the values of $R_{A4}$ provided that they may not both be hydrogen; and provided further that if either $J^6$ or $J^7$ is hydroxyl, the other may not be hydrogen or hydroxyl; and $J^8$ is selected from the group consisting of hydrogen, hydroxy, acyloxy, orthoesteroxy, ether, silyl ether and a bond with $R_{A4}$ and/or $J^6$ or $J^7$ to form a ring.

3. A compound of claim 2 selected from the group consisting of:
(i) 12-decyl-15,17-dihydrocrotophorbolone;
(ii) 12-benzylidene-15,17-dihydrocrotopborbolone;
(iii) bisdehydrophorbol 12-myristate;
(iv) 13-deoxo-13-α-hydroxybisdehydrophorbol 12-octyldimethylsilyl ether;
(v) 13-deoxo-13-α-carboxybisdehydrophorbol 12-{3',5'-bis(trifluoromethyl)phenyl}carbamate;

(vi) bisdehydrophorbol 12-octylcarbonate; and
(vii) bisdehydrophorbol 12-(3',5'-dimethoxybenzyl) carbamate.

4. A compound of claim 2 wherein formula $I_R$ carries a substituted or unsubstituted cyclopropyl ring at carbons 13 and 14, forming $I_P$

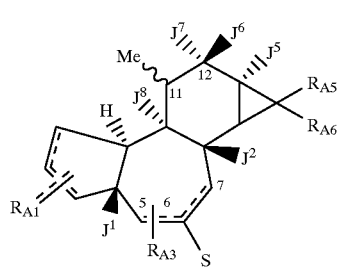

wherein the $R_{A5}$ and $R_{A6}$ moieties are independently selected from the group consisting of hydrogen, halogen and straight chain or branched chain, cyclic or acyclic, saturated or unsaturated or aromatic carbon- and/or heteroatom-containing groups, which, taken together, contain a total of not more than 30 carbon atoms, not more than 24 halogen atoms and not more than 9 heteroatoms selected from the group consisting of oxygen, nitrogen, silicon, phosphorus and sulfur.

5. A compound of claim 4 wherein, carbon 2 of $I_P$ carries a methyl group, $J^1$ is hydroxy, carbon 9 carries a hydroxy group in the α configuration, carbons 10 and 14 carry hydrogens in the α configuration, carbon 11 carries a methyl group in the α configuration and $R_{A5}$ and $R_{A6}$ are both methyl, forming $I_{PP}$:

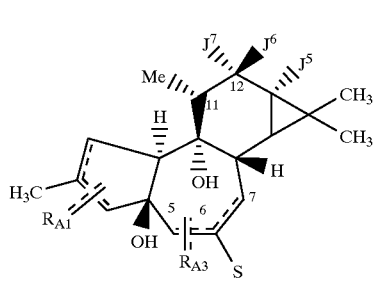

6. A compound of claim 5 comprising a phorbol 12-ester or a 12-α-phorbol 12-ester.

7. A compound of claim 5 selected from the group consisting of:
(i) 3-deoxo-3-β-hydroxyphorbol 12-{4'-(9",10"-dihydrophenanthren-2")butyrate};
(ii) 3-deoxo-3-(2',4'-difluorophenylacetoxy)-12-deoxy-12-oxophorbol;
(iii) 3-deoxo-3-(2',4'-difluorophenylacetoxy)-12-deoxy-12-oxophorbol 13-carbamate;
(iv) phorbol 12-(2',4'-difluorophenylacetate);
(v) phorbol 12-{3',5'-bis(trifluoromethyl)benzoate};
(vi) phorbol 12-{3',5'-bis(trifluoromethyl)phenylacetate};
(vii) phorbol 12-(4'-n-hexylbenzoate);
(viii) phorbol 12-(3',5'-dimethoxyphenylacetate);
(ix) phorbol 12-(4'-phenylbenzoate);
(x) phorbol 12-(pentafluorophenyl)acetate
(xi) 12-α-phorbol 12-(4'-n-hexylbenzoate);
(xii) phorbol 12-n-octadecylcarbamate;
(xiii) phorbol 12-(pentafluorophenyl)carbamate; and
(xiv) phorbol 12-{3',5'-bis(trifluoromethyl) phenylcarbamate}.

8. A compound of claim 5 wherein said compound is phorbol 12-{4'-(9",10"-dihydrophenanthrene-2')butyrate}.

9. A composition, comprising:
a physiologically acceptable pharmaceutical carrier; and
a compound, in a quantity of between about 0.001 and 3000 mg per unit dosage, of the formula I:

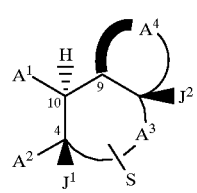

in the form of an individual isomer, an isomer mixture, a racemate or optical antipode, or a pharmaceutically acceptable salt thereof;
wherein
$A^1$ and $A^2$ may independently be selected from the group consisting of hydrogen, halogen and a straight chain or branched chain, cyclic or acyclic, saturated or unsaturated or aromatic carbon- and/or heteroatom-containing group having not more than 34 carbon atoms, not more than 24 halogen atoms and not more than 6 heteroatoms selected from the group consisting of oxygen, nitrogen, silicon, phosphorus, boron and sulfur; or,
$A^1$ and $A^2$ taken together may complete a 5- or 6-membered carbocyclic or heterocyclic ring, optionally substituted by, respectively, up to six or up to eight straight chain or branched chain, cyclic or acyclic, saturated or unsaturated or aromatic carbon- and/or heteroatom-containing groups, which groups may optionally form one or two additional rings by connection among themselves and/or to $J^1$ or $A^4$ and which, taken together, contain a total of not more than 30 carbon atoms, not more than 24 halogen atoms and not more than 9 heteroatoms selected from the group consisting of oxygen, nitrogen, silicon, phosphorus, boron and sulfur;
$A^3$ is a three atom chain which carries S and completes a 7-membered carbocyclic ring substituted by 0–5 straight chain or branched chain, cyclic or acyclic, saturated or unsaturated or aromatic carbon- and/or heteroatom-containing groups, which, taken together, excluding S, contain not more than 12 carbon atoms, not more than 8 halogen atoms, and not more than 5 heteroatoms selected from the group consisting of oxygen, nitrogen, silicon, phosphorus and sulfur; provided that, excluding S, the middle carbon atom of $A^3$ is not substituted by hydroxymethyl or 1-hydroxyethyl;
$A^4$ completes a 6-membered carbocyclic ring connected in the β configuration to carbon atom 9, substituted by 0–8 straight chain or branched chain, cyclic or acyclic, saturated or unsaturated or aromatic carbon- and/or heteroatom-containing groups, linked to $A^4$ by single or double bonds, the group or groups optionally completing 1–2 additional rings by connections among themselves and/or 1–2 additional rings by connections to $A^1$, A², a ring formed by A¹ and A² together, and/or a bond to carbon 9, wherein said groups, taken together, include not more than 50 carbon atoms, not more than 24 halogen atoms, and not more than 15 heteroatoms selected from the group consisting of oxygen, nitrogen, silicon, phosphorus, boron and sulfur; and wherein A⁴ carries at least one substituent which is not hydrogen and is not hydroxyl at carbon 12 and carries a substituent selected from the group consisting of hydroxy, unsubstituted amino, thiol, hydroxymethyl, mercaptomethyl, aminomethyl, 2-hydroxyethyl, carboxy, unsubstituted carboxamido, unsubstituted aminocarbonyloxy group, each in the α configuration on carbon 13, and an oxo or thiono group on carbon 13;

carbon atom 9 is bound to a moiety selected from the group consisting of hydrogen, hydroxy, acyloxy, orthoesteroxy, ether, silyl ether and a group attached to A⁴;

J¹ may be selected from the group consisting of hydrogen, fluoro, chloro, hydroxy, amino, mono- or di(lower-alkyl)amino, methyl, ethyl, vinyl, ethynyl, propargyl, cyano, methoxy, ethoxy, trifluoromethyl, 2-hydroxyethyl, 2-hydroxypropyl, 3-hydroxypropyl, acetoxy, propanoyloxy, acetyl, propanoyl, hydroxyacetyl, 2-hydroxypropanoyloxy, 3-hydroxypropanoyl, acetamido, propanamido, hydroxyacetamido, 2-hydroxypropanamido, and 3-hydroxypropanamido each of which must be situated in the β configuration, or J¹ taken together with A¹, A², or a ring formed by A¹ together with A² may complete a 3- to 7-membered substituted or unsubstituted carbocyclic or heterocyclic ring, the substituents of which contain not more than 15 carbon atoms, not more than 10 halogens, and not more than 8 heteroatoms selected from the group consisting of oxygen, nitrogen, silicon, phosphorus, boron and sulfur;

J² is selected from the group consisting of hydrogen, methyl, ethyl, hydroxymethyl, hydroxyethyl, vinyl, ethynyl, allyl, propargyl, n-propyl and isopropyl; and S is bound to carbon 6 and is selected from the group consisting of hydroxymethyl, 1-hydroxyethyl and 2-hydroxy-2-propyl.

10. A composition of claim 9 wherein formula I is I$_R$:

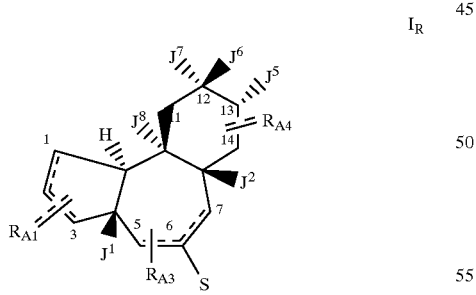

I$_R$ wherein carbons 1 and 2 or carbons 2 and 3 may be joined by a double bond;

carbons 5 and 6 or carbons 6 and 7 may be joined by a double bond;

R$_{A1}$ represents not more than 6 identical or different substituents bonded independently via single and/or double bonds to carbons 1, 2 and/or 3, which substituents may optionally form one or two additional rings by connection among themselves and/or to J¹ or substituents on the 6-membered ring and which may independently be selected from the group consisting of hydrogen, halogen and straight chain or branched chain, cyclic or acyclic, saturated or unsaturated or aromatic carbon- and/or heteroatom-containing groups, which, taken together, contain a total of not more than 30 carbon atoms, not more than 24 halogen atoms and not more than 9 heteroatoms selected from the group consisting of oxygen, nitrogen, silicon, phosphorus and sulfur;

R$_{A3}$ represents not more than 5 identical or different substituents bonded independently via single and/or double bonds to carbons 5, 6 and/or 7, which substituents are independently selected from the group consisting of hydrogen, halogen and straight chain or branched chain, cyclic or acyclic, saturated or unsaturated or aromatic carbon- and/or heteroatom-containing groups, which, taken together, contain not more than 12 carbon atoms, not more than 8 halogen atoms, and not more than 5 heteroatoms selected from the group consisting of oxygen, nitrogen, silicon, phosphorus and sulfur;

R$_{A4}$ represents not more than 5 identical or different substituents bonded independently via single or double bonds to carbons 11, 12, 13 and/or 14, which substituents may independently be selected from the group consisting of hydrogen, halogen and straight chain or branched chain, cyclic or acyclic, saturated or unsaturated or aromatic carbon- and/or heteroatom-containing groups, said group or groups optionally completing 1–3 additional rings through bonds among themselves and/or 1–5 additional rings when taken together with the 5-membered ring and/or its substituent(s) R$_{A1}$ and/or J⁸, and which halogen(s) and groups, taken together, include not more than 50 carbon atoms, not more than 24 halogen atoms, and not more than 15 heteroatoms selected from the group consisting of oxygen, nitrogen, silicon, phosphorus and sulfur;

J⁵ is selected from the group consisting of a hydroxy, amino, thiol, hydroxymethyl, mercaptomethyl, aminomethyl, 2-hydroxyethyl, carboxy, unsubstituted carboxamido, unsubstituted aminocarbonyloxy groups each in the α configuration on carbon 13, and an oxo or thiono group doubly bonded to carbon 13;

the substituents on carbon 12, J⁶ and J⁷, may have the values of R$_{A4}$, provided that they may not both be hydrogen; and provided further that if either J⁶ or J⁷ is hydroxyl, the other may not be hydrogen or hydroxyl; and J⁸ is selected from the group consisting of hydrogen, hydroxy, acyloxy, orthoesteroxy, ether, silyl ether and a bond with R$_{A4}$ and/or J⁶ or J⁷ to form a ring.

11. A composition of claim 10 wherein the compound is selected from the group consisting of:

(i) 12-decyl-15,17-dihydrocrotophorbolone;
(ii) 12-benzylidene-15,17-dihydrocrotophorbolone;
(iii) bisdehydrophorbol 12-myristate;
(iv) 13-deoxo-13-α-hydroxybisdehydrophorbol 12-octyldimethylsilyl ether;
(v) 13-deoxo-13-α-carboxybisdehydrophorbol 12-{3',5'-bis(trifluoromethyl)phenyl}carbamate;
(vi) bisdehydrophorbol 12-octylcarbonate; and
(vii) bisdehydrophorbol 12-(3',5'-dimethoxybenzyl) carbamate.

12. A composition of claim 10 wherein formula $I_R$ carries a substituted or unsubstituted cyclopropyl ring at carbons 13 and 14, forming $I_P$

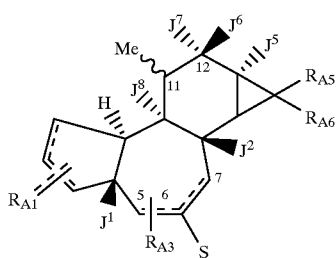

$I_P$ wherein the $R_{A5}$ and $R_{A6}$ moieties are independently selected from the group consisting of hydrogen, halogen and straight chain or branched chain, cyclic or acyclic, saturated or unsaturated or aromatic carbon- and/or heteroatom-containing groups, which, taken together, contain a total of not more than 30 carbon atoms, not more than 24 halogen atoms and not more than 9 heteroatoms selected from the group consisting of oxygen, nitrogen, silicon, phosphorus and sulfur.

13. A composition of claim 12 wherein, carbon 2 of $I_P$ carries a methyl group, $J^1$ is hydroxy, carbon 9 carries a hydroxy group in the α configuration, carbons 10 and 14 carry hydrogens in the α configuration, carbon 11 carries a methyl group in the α configuration and $R_{A5}$ and $R_{A6}$ are both methyl, forming $I_{PP}$:

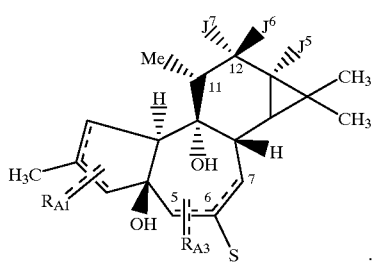

$I_{PP}$

14. A composition of claim 13 wherein the compound is selected from the group consisting of:
(i) 3-deoxo-3-β-hydroxyphorbol 12-{4'-(9",10"-dihydrophenanthren-2")butyrate};
(ii) 3-deoxo-3-(2',4'-difluorophenylacetoxy)-12-deoxy-12-oxophorbol;
(iii) 3-deoxo-3-(2',4'-difluorophenylacetoxy)-12-deoxy-12-oxophorbol 13-carbamate;
(iv) phorbol 12-(2',4'-difluorophenylacetate);
(v) phorbol 12-{3',5'-bis(trifluoromethyl)benzoate};
(vi) phorbol 12-{3',5'-bis(trifluoromethyl)phenylacetate};
(vii) phorbol 12-(4'-n-hexylbenzoate);
(viii) phorbol 12-(3',5'-dimethoxyphenylacetate);
(ix) phorbol 12-(4'-phenylbenzoate);
(x) phorbol 12-{(pentafluorophenyl)acetate};
(xi) 12-α-phorbol 12-(4'-n-hexylbenzoate);
(xii) phorbol 12-n-octadecylcarbamate;
(xiii) phorbol 12-(pentafluorophenyl)carbamate; and
(xiv) phorbol 12-{3',5'-bis(trifluoromethyl) phenylcarbamate}.

15. A composition of claim 13 wherein the compound comprises a phorbol 12-ester or a 12-α-phorbol 12-ester.

16. A composition of claim 13 wherein the compound is phorbol 12-{4'-(9",10"-dihydrophenanthrene-2')butyrate}.

17. A method for treating a mammal infected with a virus which comprises administering to a mammal in need of such treatment an antivirally effective quantity of a composition of claim 9.

18. The method of claim 17 wherein said virus is a retrovirus.

19. The method of claim 18 wherein said retrovirus comprises any Human Immunodeficiency Virus.

20. A method for treating a mammal in need of anti-inflammatory or anti-psoriatic treatment which comprises administering to a mammal in need of such treatment an effective anti-inflammatory or anti-psoriatic quantity of a composition of claim 9.

21. A method for treating a mammal in need of anti-leukemic or anti-melanoma treatment which comprises administering to a mammal in need of such treatment an effective anti-leukemic or anti-melanoma quantity of a composition of claim 9.

22. A method for treating a mammal suffering from Alzheimer's disease which comprises administering to a mammal in need of such treatment an effective anti-Alzheimer's quantity of a composition of claim 9.

23. A method for modulating protein kinase C activity comprising the step of contacting protein kinase C, in vitro or in vivo, with a composition of claim 9.

* * * * *